(12) United States Patent
Tal et al.

(10) Patent No.: US 9,149,629 B2
(45) Date of Patent: Oct. 6, 2015

(54) ESOPHAGEAL STIMULATION DEVICES AND METHODS

(75) Inventors: Michael Gabriel Tal, Savyon (IL); Dvir Keren, Tel Aviv (IL); Amichay Haim Gross, Herzliya (IL)

(73) Assignee: E-MOTION MEDICAL LTD., Tel Aviv (IL)

( * ) Notice: Subject to any disclaimer, the term of this patent is extended or adjusted under 35 U.S.C. 154(b) by 0 days.

(21) Appl. No.: 13/533,805

(22) Filed: Jun. 26, 2012

(65) Prior Publication Data

US 2013/0006323 A1      Jan. 3, 2013

Related U.S. Application Data

(60) Provisional application No. 61/501,338, filed on Jun. 27, 2011, provisional application No. 61/612,072, filed on Mar. 16, 2012.

(51) Int. Cl.
*A61N 1/372* (2006.01)
*A61N 1/05* (2006.01)
*A61N 1/36* (2006.01)

(52) U.S. Cl.
CPC .......... *A61N 1/0517* (2013.01); *A61N 1/36007* (2013.01)

(58) Field of Classification Search
CPC ......................... A61N 1/0517; A61N 1/36007
USPC .......................................................... 607/40
See application file for complete search history.

(56) References Cited

U.S. PATENT DOCUMENTS

| 4,735,206 | A | | 4/1988 | Hewson |
| 5,716,385 | A | * | 2/1998 | Mittal et al. ................ 607/40 |
| 5,814,092 | A | * | 9/1998 | King ........................... 607/46 |
| 6,010,453 | A | * | 1/2000 | Fiddian-Green ........... 600/309 |
| 6,097,984 | A | * | 8/2000 | Douglas ...................... 607/40 |
| 6,148,222 | A | * | 11/2000 | Ramsey, III ............... 600/380 |
| 6,591,137 | B1 | * | 7/2003 | Fischell et al. ............. 607/40 |
| 6,754,536 | B2 | * | 6/2004 | Swoyer et al. .............. 607/40 |
| 6,773,452 | B2 | * | 8/2004 | Shaker ....................... 600/587 |
| 7,167,750 | B2 | * | 1/2007 | Knudson et al. ........... 607/40 |

(Continued)

FOREIGN PATENT DOCUMENTS

| WO | WO 2006/060458 | 6/2006 |
| WO | WO 2012/131303 | 10/2012 |
| WO | WO 2014/105759 | 7/2014 |

OTHER PUBLICATIONS

International Search Report and Written Opinion dated Oct. 30, 2012 received in PCT Application No. PCT/IB2012/001546.

(Continued)

*Primary Examiner* — Carl H Layno
*Assistant Examiner* — Erin Piateski
(74) *Attorney, Agent, or Firm* — Clements Bernard PLLC; Christopher L. Bernard; Lawrence A. Baratta, Jr.

(57) ABSTRACT

Systems for stimulating one or more esophageal muscle contractions are provided. The systems, which are designed to evoke esophageal motion to promote the downward movement of material, include an elongated member for placement in a patient's esophagus and at least one mechanical or electrical stimulator coupled to the elongated member. Methods for stimulating and contracting an esophageal muscle using electrodes and a generated signal sequence are also provided.

27 Claims, 17 Drawing Sheets

(56) References Cited

U.S. PATENT DOCUMENTS

| | | | |
|---|---|---|---|
| 7,738,961 B2* | 6/2010 | Sharma | 607/40 |
| 2001/0053920 A1* | 12/2001 | Shaker | 606/197 |
| 2006/0265021 A1 | 11/2006 | Herbert | |
| 2007/0185540 A1* | 8/2007 | Ben-Haim et al. | 607/40 |
| 2007/0225576 A1* | 9/2007 | Brown et al. | 600/301 |
| 2007/0225617 A1* | 9/2007 | Mabary et al. | 600/587 |
| 2007/0293926 A1* | 12/2007 | Dunlay et al. | 607/148 |
| 2008/0009810 A1* | 1/2008 | Hamdy | 604/265 |
| 2008/0167675 A1* | 7/2008 | Hogosta et al. | 606/196 |
| 2008/0249507 A1* | 10/2008 | Hadani | 604/523 |
| 2008/0312712 A1* | 12/2008 | Penner | 607/40 |
| 2008/0319504 A1* | 12/2008 | Loushin et al. | 607/40 |
| 2009/0018602 A1* | 1/2009 | Mitelberg et al. | 607/40 |
| 2009/0030475 A1* | 1/2009 | Brynelsen et al. | 607/40 |
| 2009/0062725 A1* | 3/2009 | Goebel | 604/28 |
| 2009/0132001 A1* | 5/2009 | Soffer et al. | 607/40 |
| 2009/0143651 A1* | 6/2009 | Kallback et al. | 600/301 |
| 2009/0259274 A1 | 10/2009 | Simon et al. | |
| 2010/0087715 A1* | 4/2010 | Van Bommel et al. | 600/301 |
| 2010/0160996 A1 | 6/2010 | Simon et al. | |
| 2010/0305655 A1* | 12/2010 | Raffle et al. | 607/40 |
| 2011/0004266 A1* | 1/2011 | Sharma | 607/40 |
| 2011/0034967 A1* | 2/2011 | Chen et al. | 607/40 |
| 2011/0130650 A1* | 6/2011 | Dayan et al. | 600/424 |
| 2011/0144481 A1* | 6/2011 | Feer et al. | 600/424 |

OTHER PUBLICATIONS

Lee et al., "Changes in gastroesophageal reflux in patients with nasogastric tube followed by percutaneous endoscopic gastrostomy," *J. Formos Med Assoc* 2011; 110(2): 115-19.

Manning et al., "Nasogastric intubation causes gastroesophageal reflux in patients undergoing elective laparotomy," *Surgery* 2001; 130(5): 788-91.

Torres et al., "Stomach as a source of colonization of the respiratory tract during mechanical ventilation: association with ventilator-associated pneumonia," *European Respiratory Journal* 1996; 9(8): 1729-35.

Ibanez et al., "Gastroesophageal reflux in intubated patients receiving enteral nutrition: effect of supine and semirecumbent positions," *Journal of Parenteral and Enteral Nutrition* 1992; 16(5): 419-22.

Pellegrini et al., "Gastroesophageal reflux and pulmonary aspiration: incidence, functional abnormality, and results of surgical therapy," *Surgery* 1979; 86(1): 110-19.

International Preliminary Report on Patentability dated Jan. 7, 2014 for PCT Application No. PCT/IB2012/001546.

International Search Report and Written Opinion dated Jun. 20, 2014 for PCT Application No. PCT/US2013/077261.

Paterson: "Esophageal peristalsis", GI Motility online. Retrieved from internet URL: http://www.nature.com/gimo/contents/ptl/full/gimo13/html on Mar. 5, 2014.

\* cited by examiner

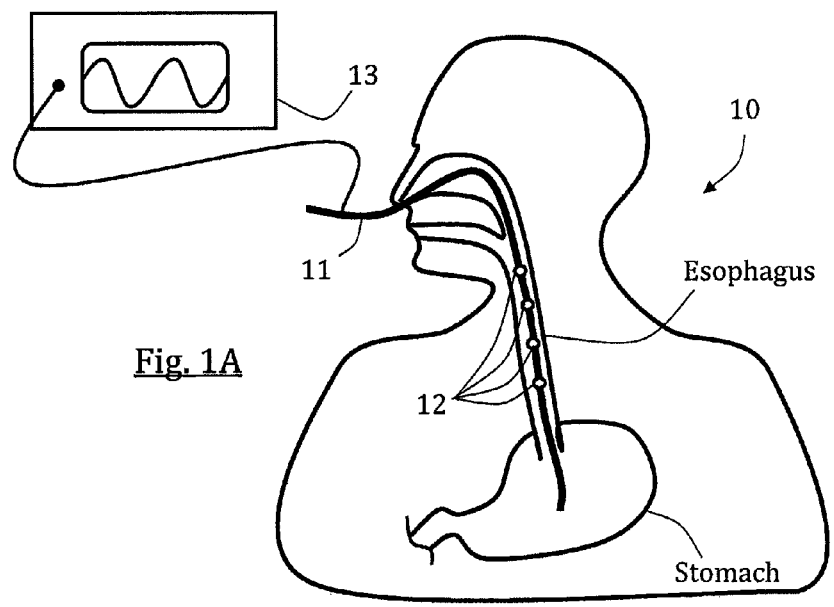
Fig. 1A
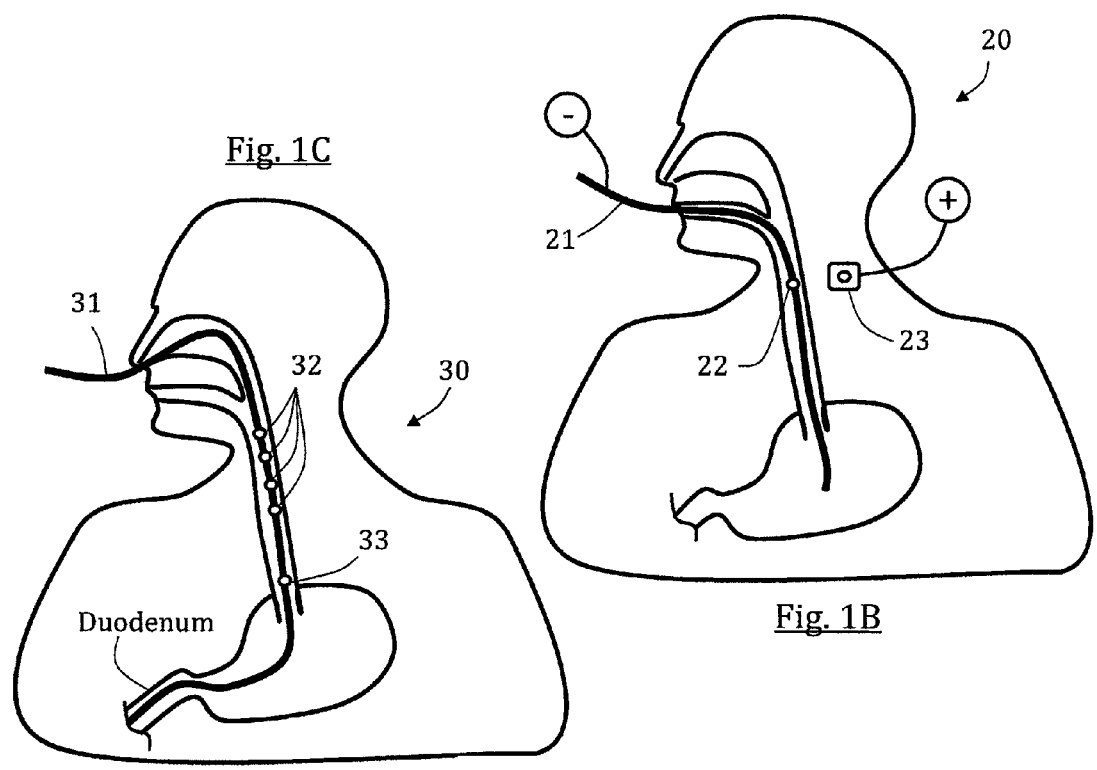
Fig. 1C
Fig. 1B

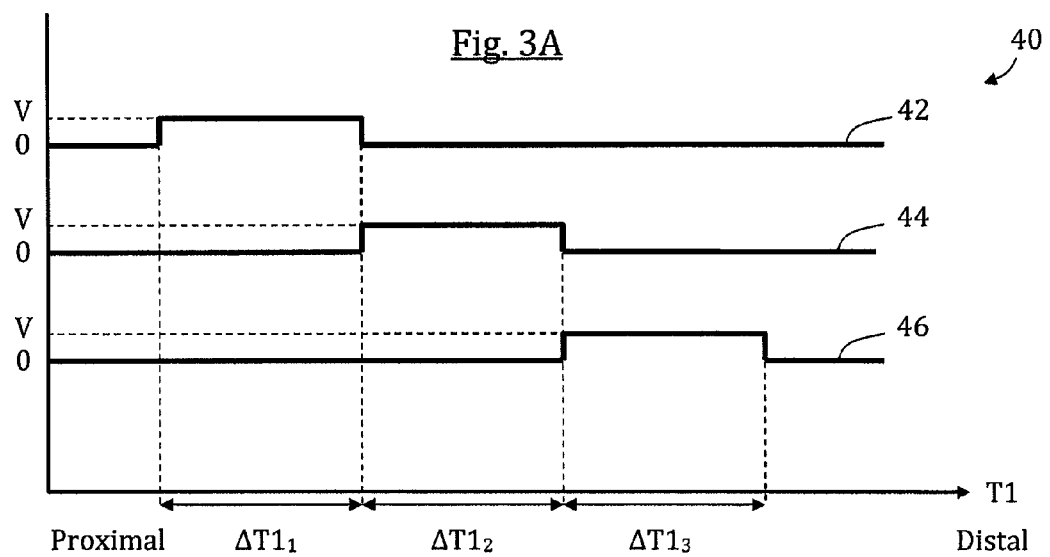

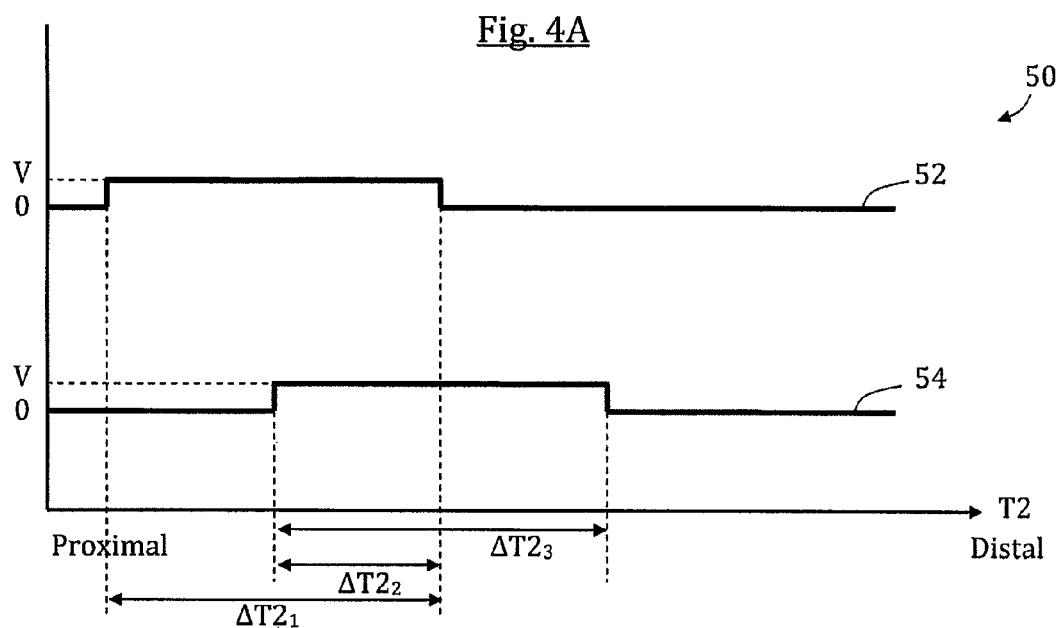

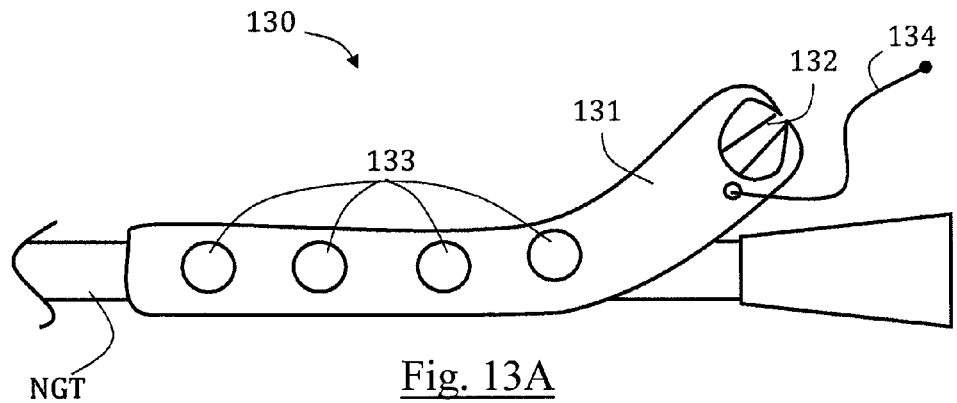
Fig. 13A
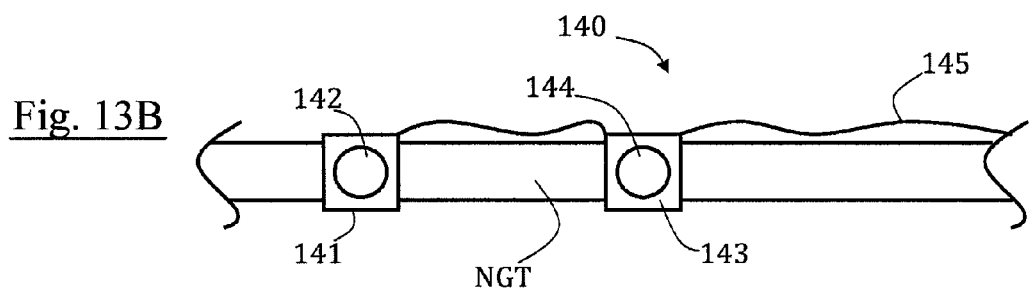
Fig. 13B
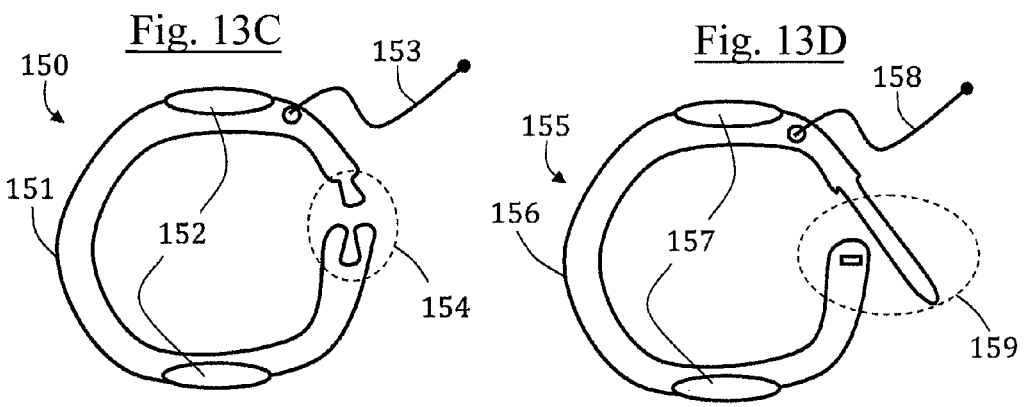
Fig. 13C
Fig. 13D

ESOPHAGEAL STIMULATION DEVICES AND METHODS

CROSS-REFERENCE TO RELATED APPLICATIONS

This application claims priority to U.S. Provisional Patent Application No. 61/501,338, filed Jun. 27, 2011, and U.S. Provisional Patent Application No. 61/612,072, filed Mar. 16, 2012, both entitled "ESOPHAGEAL STIMULATION DEVICE", the disclosures of which are fully incorporated herein by reference as if fully set forth herein.

BACKGROUND

1. Field of the Invention

The present invention, in some embodiments thereof, relates to devices and methods for generating motility in GI organs, and in particular to devices and methods for generating esophageal motility for diminishing retrograde flow of gastric contents.

2. Description of the Related Art

The esophagus is a tubular muscular organ having a length of approximately 25 cm, located between the upper esophageal sphincter (UES) and the lower esophageal sphincter (LES). The esophagus functions solely to deliver food from the mouth to the stomach using peristaltic muscle motion. Peristalsis is a sequential, coordinated contraction wave that travels the entire length of the esophagus, propelling intraluminal contents distally to the stomach. Primary peristalsis is the peristaltic wave triggered by the swallowing center. The peristaltic contraction wave travels at a speed of approximately 2 cm/s and correlates with manometry-recorded contractions. The secondary peristaltic wave is induced by esophageal distension from the retained bolus, refluxed material, or swallowed air, with the primary role to clear the esophagus of retained food or any gastroesophageal refluxate. Tertiary contractions are simultaneous, isolated, dysfunctional contractions. Anesthetization or sedation are suspected of causing suspension of esophageal peristaltic motility and lowers LES pressure, hence gastric content are more prone to infiltrate and travel proximally in the esophagus.

Gastric contents refluxing through the esophagus are known to affect conditions which may increase morbidity and mortality rates. Gastroesophageal Reflux (GER) is a condition, in which the LES opens spontaneously, for varying periods of time, or does not close properly and stomach contents rise up into the esophagus. In Laryngopharyngeal Reflux (LPR), the retrograde flow of gastric contents reaches the upper aero-digestive tract. In order to diminish and treat such conditions, efforts have been made to develop medical and surgical means for improving LES functionality and for creating a substitute sphincter proximally adjacent the stomach. In some occasions it may be advantageous to develop a second "line of defense" provided proximally to the LES along the esophagus, especially to push back any gastric contents or chyme that infiltrated the LES or any substitute or supplement thereof. Such a need may arise, for example, in cases of intubation and/or ventilation, usually in anesthetized ICU patients, CVA patients, or others, in which esophageal motility is muted or less dominant.

Tubefeeding (e.g., "gastric feeding" or "enteral feeding") is a common and life preserving procedure, however complications can arise. GER is commonly associated with tube-feeding, including in usage of nasogastric tubing (NGT) and other gastric feeding practices. Research in past years has discussed the emergence of GER as an effect of the use of NGT (see for example in Ibanez et al., "Gastroesophageal reflux in intubated patients receiving enteral nutrition: effect of supine and semirecumbent positions", *JPEN J Parenter Enteral Nutr.* 1992 September-October; 16(5):419-22; in Manning et al., "Nasogastric intubation causes gastroesophageal reflux in patients undergoing elective laparotomy", *Surgery.* 2001 November; 130(5):788-91; and in Lee et al., "Changes in gastroesophageal reflux in patients with nasogastric tube followed by percutaneous endoscopic gastrostomy", *J Formos Med Assoc.* 2011 February; 110(2):115-9).

Pulmonary aspiration is the entry of material from the oropharynx or gastrointestinal tract into the larynx and lower respiratory tract. Consequences of pulmonary aspiration range from no injury at all, to chemical pneumonitis or pneumonia, to death within minutes from asphyxiation. One common cause of pulmonary aspiration is aspiration of gastric contents, as suggested in relevant literature (see for example Pellegrini et al., "Gastroesophageal reflux and pulmonary aspiration: incidence, functional abnormality, and results of surgical therapy", *Surgery.* 1979 July; 86(1):110-9, indicating that incidence of aspiration is due to a motor disorder that interferes with the ability of the esophagus to clear refluxed acid, and that abnormal pulmonary symptoms can induce or result from gastroesophageal reflux).

Ventilator-associated pneumonia (VAP) is pneumonia that develops 48 hours or longer after mechanical ventilation is given by means of an endotracheal tube or tracheostomy. VAP results from the invasion of microorganisms into the lower respiratory tract and lung parenchyma. Intubation compromises the integrity of the oropharynx and trachea and allows oral and gastric secretions to enter the lower airways. The aetiopathogenesis of VAP requires abnormal oropharyngeal and gastric colonization and the further aspiration of their contents to the lower airways. Known risk factors for gastric colonization include: alterations in gastric juice secretion; alkalinization of gastric contents; administration of enteral nutrition; administration of antacids; and the presence of bilirubin. According to Torres et al. (in "Stomach as a source of colonization of the respiratory tract during mechanical ventilation: association with ventilator-associated pneumonia", *Eur Respir J.* 1996 August; 9(8):1729-35), although the role of the colonized gastric reservoir in the development of VAP remains debatable, there is major evidence in the literature in favor of the gastric origin of part of these pulmonary infections.

US Patent Application No. 2011/0130650 relates to an enteral feeding device comprising "expandable means which prevents or significantly reduces aspirations from the alimentary tract to the respiratory system. In further aspects, the invention relates to systems comprising said enteral feeding device, methods and uses thereof."

US Patent Application No. 2010/0160996 " relates to methods and apparatuses for treating ailments by "inserting a balloon-electrode device into an esophagus of a mammal, the balloon-electrode device including: (i) a nasogastral (NG) tube having an internal passageway and an external surface, (ii) at least one electrode coupled to the external surface of the NG tube, (iii) a conductor extending through the internal passageway of the NG tube and electrically connecting to the electrode, and (iv) a balloon surrounding the electrode and a portion of the NG tube; inflating the balloon with fluid such that the electrode is substantially centrally located within an interior volume of the balloon; and applying at least one electrical signal to the electrode via the conductor such that an electromagnetic field emanates from the electrode to at least one of nerves and muscles of the mammal."

US Patent Application No. 2008/0249507 relates to a "food administering apparatus including a feeding tube, having a distal outlet and proximal inlet, adapted for insertion of the distal outlet into the stomach of an adult patient while the proximal inlet is outside the patient, the tube being suitable for administering food or medicine from a proximal port to the distal outlet and at least one electrode mounted on the tube."

SUMMARY

According to an aspect of some embodiments of the present invention, there is provided a system for evoking esophageal motion. In some embodiments, the esophageal motion includes at least one local contraction. In some such embodiments, at least one local contraction decreases a local segment of the esophagus lumen, optionally to at least 50% its initial diameter. In another embodiment, the at least one local contraction fully closes a local segment of the esophagus. In some embodiments, at least one local contraction develops a local esophageal pressure of at least 15 mmHg, and optionally at least 25 mmHg, or higher, or lower or intermediate to said values.

In some embodiments, the esophageal motion is a patterned motion including at least two evoked contractions at different esophageal portions. Optionally, the different esophageal portions include adjacent esophageal portions and/or remote esophageal portions. In some embodiments, the at least two evoked contractions are sequentially and/or timely generated according to a preset sequence. In some embodiments, the esophageal motion includes a distally advancing contraction wave, optionally though not necessarily including peristalsis. In some embodiments, use of such a system and/or method of esophageal stimulation diminishes retrograde flow of stomach contents. In some cases, such a method accomplishes this result by stimulating the esophagus to produce a distally travelling wave of contractions that simulate natural peristalsis.

In some embodiments, the system for evoking esophageal motion includes an elongated member sized and configured for nasal or oral placement in a patient's esophagus. In some embodiments, the elongated member is a medical intubation device, and optionally, a gastric feeding tube.

In some embodiments, the system further includes at least one stimulator mounted or mountable on the elongated member, adapted to stimulate a chosen portion of the esophagus to evoke a local shaped contractive reaction. Optionally, the at least one stimulator is fixed to the elongated member. In some embodiments, alternatively or additionally, the at least one stimulator is provided with a fixator configured for mounting the at least one stimulator on a chosen external portion of the elongated member. The fixator may be slidably movable along a length of the elongated member, optionally restrainedly securable around the chosen external portion of the elongated member, and/or optionally fixedly lockable to the chosen external portion of the elongated member thereby preventing sliding therealong.

In some embodiments, the at least one stimulator includes at least two stimulators sequentially positioned along an esophageal length; each stimulator is configured to stimulate a different esophageal portion. Optionally, a plurality of stimulators is provided along the effective length of the medical intubation device. In some embodiments, a distance of less than 5 cm exists between at least two of the stimulators, and a distance of greater than 10 cm exists between a proximal most stimulator and a distal most stimulator.

In some embodiments, the at least one stimulator includes an electrode, or a plurality of electrodes, for allowing local electrical stimulation(s) of muscle tissue and/or neural tissue, adjacent and/or in direct contact. The electrode(s) may be shaped as chosen or needed, as known in the relevant art, and may be, for example, circular, rectangular, or ring shaped.

In some embodiments, the at least one stimulator includes an expandable member, which is optionally a mechanical stimulator, optionally inflatable, and sized and/or shaped when expanded to radially stretch out an esophageal portion in a manner that evokes a shaped contractive reaction distal to the esophageal portion.

In some embodiments, the system further includes a generator connected to the at least one stimulator. The generator may be provided outside the patient body or alternatively be sized and configured for prolonged intra-oral or intra-esophageal placement. The generator may be an electrical signal generator adapted to generate electrical stimulations via at least one electrode or at least two electrodes electrically connected thereto. Alternatively, the generator may include a pump for cases of inflatable stimulators. The generator may be a pulse generator and/or may be able to generate different shaped signals, for example a step wave, a sine wave, a saw-tooth wave, a variable width pulse or any combination thereof. The generator may include or be connectable to a power source, which may or may not comprise an element of the system. In some embodiments, the power source may be sized and configured for prolonged intra-oral or intra-esophageal placement.

In some embodiments of the invention, the system further includes at least one sensor mounted or mountable on the elongated member. The at least one sensor may be mounted distally to a distal-most stimulator. Optionally, a proximal-most sensor is positioned at least 5 cm distally to the distal-most stimulator, optionally at least 10 cm, optionally approximately 20 cm, or higher, or lower, or intermediate to said values. In some embodiments, the at least one sensor comprises at least one of: a pH sensor, a pressure sensor, a manometer, an impedance sensor, a motion sensor, a capacitance sensor and a mechanical sensor.

In some embodiments, the system for evoking esophageal motion includes a catheter and a controller, wherein the catheter and controller are configured for wired or wireless communication with each other. The catheter includes a plurality of electrodes and at least one pH sensor. In some embodiments, the controller is configured and programmed to initiate an electrical stimulation via at least one of the plurality of electrodes in response to at least one pH sensor sensing a local pH less than 3. In use, the at least one pH sensor of various embodiments senses local pH in real-time, and at least one of the plurality of electrodes is stimulated upon the at least one pH sensor sensing a local pH below 3 in real-time. In some embodiments, the plurality of electrodes and the one or more pH sensors are arranged such that upon a pH sensor sensing a local pH less than 3, one or more electrodes positioned proximally to the pH sensor are stimulated.

In an aspect of some embodiments, there is provided a method for generating esophageal motion. In some embodiments, the method comprises a step of positioning at least two electrodes, including a proximally positioned electrode and a distally positioned electrode, at distant portions along the esophagus. Optionally, the method includes also a step of electrically connecting the at least two electrodes to a generator. Optionally, the method further includes a step of generating a signal sequence including a first signal at the proximally positioned electrode thereby stimulating a proximal esophageal tissue and a second signal at the distally positioned electrode thereby stimulating a distal esophageal tissue. In some embodiments, the signal sequence produces a contraction wave that travels a length of the esophagus.

Optionally, additionally or alternatively, a method for generating esophageal motion with the system will include a step of placing in an esophagus the elongated member and at least one electrode mountable thereon, and generating at least one stimulating signal to evoke a local shaped contractive reaction. The local shaped contractive reaction may be a spasm, a full contraction, a partial contraction, a peristalsis or any combination thereof.

A method for connecting at least one electrode to a gastric tube pre-positioned in a patient's esophagus may include a step of locating a target portion on the gastric tube at a chosen distance from a proximal end thereof. Optionally, the method also includes a step of providing an electrode fixator configured for fixedly covering a portion of the gastric tube. Optionally, the electrode fixator comprises at least one electrode electrically connectable with a signal generator and locking means. Optionally, the method also includes a step of positioning the electrode fixator over the target portion. Optionally, the positioning includes sleeving the electrode fixator over and along the gastric tube. (Hereinafter, sleeving is defined as sliding a sleeve, sock, or other tubular-shaped element, rigid or nonrigid, over, around, and along an object, so as to at least partially encase said object.) Optionally, the method also includes a step of applying the locking means to fixedly lock the electrode fixator in place. In some embodiments, the gastric tube may be partially withdrawn to expose the target portion.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of various embodiments. In this regard, the description taken with the drawings makes apparent to those skilled in the art how embodiments of the invention may be practiced. In the drawings:

FIG. 1A schematically illustrates an exemplary nasogastric tube positioned in a patient's esophagus and including a plurality of stimulators, in accordance with an embodiment of the present invention;

FIG. 1B schematically illustrates an exemplary oral feeding tube positioned in a patient's esophagus and including a mono-polar stimulator, in accordance with an embodiment of the present invention;

FIG. 1C schematically illustrates an exemplary feeding tube positioned in a patient's esophagus and including a plurality of stimulators and a sensor, in accordance with an embodiment of the present invention;

FIGS. 3A-D schematically illustrate a first exemplary stimulation sequence and a correspondingly generated patterned esophageal motion, in accordance with some embodiments of the present invention;

FIGS. 4A-D schematically illustrate a second exemplary stimulation sequence and a correspondingly generated patterned esophageal motion, in accordance with some embodiments of the present invention;

FIGS. 13A-D schematically illustrate different exemplary fixators, in accordance with some embodiments of the present invention;

DETAILED DESCRIPTION OF CERTAIN EMBODIMENTS

Figure 2A:
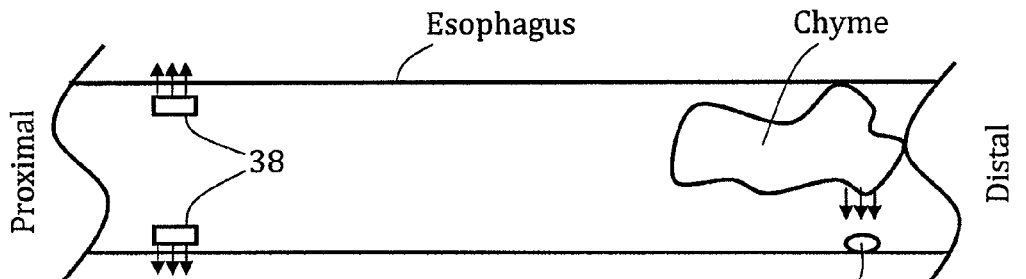
FIGS. 2A-C schematically illustrate a partial cut view of a contraction wave stimulating system provided in an esophagus, shown at different operation stages, in accordance with some embodiments of the present invention.

The following preferred embodiments may be described in the context of exemplary esophageal stimulation procedures for ease of description and understanding. However, the invention is not limited to the specifically described devices and methods, and may be adapted to various clinical applications without departing from the overall scope of the invention. For example, devices and related methods including concepts described herein may be used for stimulating other GI organs such as but not limited to the: stomach wall, duodenum, jejunum, ileum, caecum, small intestine, colon, large intestine, throat and gullet.

The present invention, in some embodiments thereof, relates to devices and methods for generating motility in GI organs, and in particular to devices and methods for generating, at least, esophageal motility for diminishing retrograde flow of gastric contents.

An aspect of some embodiments relates to a system for generating a patterned esophageal motion. A patterned esophageal motion may be any local or cross-esophageal muscular expansion or contraction, or any combination thereof, evoked and/or orchestrated following generated stimulation. The pattern may be a chosen shape and/or magnitude of a local esophagus contraction and/or a distally progressive contraction wave having chosen characteristics, including but not limited to contraction force, wave travel velocity and wave occurrence frequency. In some embodiments, the patterned esophageal motion includes peristalsis, optionally simulating a naturally occurring esophageal peristalsis or creating a synthetic peristalsis based on an algorithmic sequence of stimulations, and/or any combination of local contractions, distally progressive contraction wave and/or selectively evoked naturally occurring peristalsis at a patient's esophagus.

In some embodiments, the system includes at least one stimulator adapted to stimulate a portion of the esophagus to evoke a shaped contractive reaction. In some embodiments, the at least one stimulator includes an expandable, optionally inflatable, member, sized and/or shaped when expanded to radially stretch out an esophageal portion in a manner that evokes a shaped contractive reaction distal to the esophageal portion. An inflatable stimulator may be connected to a pump, optionally hydraulic or pneumatic, and may be selectively inflated or deflated according to a chosen scheme, such as, for example, a predetermined and/or programmed scheme, and optionally a scheme including pulsatory actuation.

Optionally, alternatively or additionally, the at least one stimulator includes an electrode configured for electrical stimulation of adjacent/contacting esophagus muscle tissue. A stimulating electrode may be connectable or provided readily connected with a generator, optionally a pulse generator, configured to generate a chosen sequence of stimulations. Optionally, alternatively or additionally, an internal power and/or signal source may be provided with the system that is sized and configured for intra-body (e.g., intra-orally) placement, optionally in or adjacent the esophagus. In some other optional embodiments, a power and/or signal source may be provided (e.g., worn) on the patient. In some exemplary embodiments, at least one electrode and/or sensor is connected with such an internal power source sized and configured for placement on a medical intubation device (e.g., a feeding tube).

In some embodiments, the system includes a plurality of stimulators provided at different relative locations within the esophagus.

A local contraction of the esophagus, or any combination or pattern of esophageal contractions may increase local and/or average esophageal pressure. Optionally, alternatively or additionally, stimulation is used to decrease local and/or average volume entrapped along the esophagus lumen between the LES and the UES thereby increasing local and/or average pressure. By increasing the pressure at a local segment of the esophagus lumen, a retrograded material or chyme may be forced to travel backward to a distal lumen segment being less pressured, whereas by increasing the average or overall pressure in the esophagus, a possible reflux causing positive pressure difference between the stomach and the esophagus may be diminished and even reversed, thereby diminishing the possibility or volume of refluxed material or even preventing reflux. In some embodiments, a local and/or average pressure caused by a single evoked contraction or a series of evoked contractions may be equal or higher than 15 mmHg, optionally equal or higher than 25 mmHg, optionally equal or higher than 50 mmHg, and optionally equal or higher than 100 mmHg, or lower, higher, or intermediate to any of said values.

In some embodiments, the system further includes, is provided with, or is connected to a medical intubation device that is sized and configured for nasal or oral placement in a patient's esophagus. In some embodiments, the medical intubation device is a gastric feeding tube.

In some embodiments, at least one stimulator is fixed to the medical intubation device. Optionally, alternatively or additionally, at least one stimulator is provided with a fixator configured for fixedly covering a portion of the medical intubation device. The fixator may be slidably movable along a length of the medical intubation device and/or may be restrainedly securable around the portion of the medical intubation device. In some embodiments, the fixator is fixedly lockable to the portion of the medical intubation device thereby preventing sliding therealong.

A fixator may be sleeved and/or otherwise coupled to the medical intubation device after the latter has been partially or fully withdrawn from a patient's esophagus or trachea. Alternatively, a fixator may be mounted on to a medical intubation device prior to initial placement in the patient. A proper location of a fixator and/or stimulator may be achieved under imagery guidance (e.g., x-ray). Optionally, alternatively or additionally, means (e.g., recesses, indentations, etc.) are provided or created on portions of the medical intubation device to allow controlled positioning by engaging the fixator/stimulator thereto. In cases in which the medical intubation device is kept in place within the patient, means may be applied to distally advance a fixator/stimulator along and over the medical intubation tube's outer periphery to a chosen location, optionally under x-ray monitoring.

In some embodiments, the at least one stimulator includes at least two stimulators sequentially positioned along an esophageal length, each stimulator being configured to stimulate a different esophageal portion. Optionally, a plurality of stimulators is provided along the effective length of the medical intubation device.

In some embodiments wherein the at least one stimulator comprises a plurality of electrodes, the electrodes are arranged in groups referred to herein as terminals. In some embodiments, two electrodes form a terminal. In some such embodiments, one electrode is a positive electrode, which receives current from a signal generator, and the other electrode is a negative electrode, which is grounded. The distance between each terminal may be fixed or variable, and the terminals are spaced such that the distance between each terminal is greater than the distance between each electrode within any given terminal. For example, the width of the terminal (i.e., the distance between the electrodes of a terminal) may be 5-10 mm, and optionally 8 mm. The distance between each terminal may be 15-30 mm, optionally 20 mm, or optionally, below, above, or intermediate to said values. In other embodiments having two electrodes per terminal, the system also comprises an array of controlled relays coupled to the electrodes. The array of controlled relays may be configured to selectively transition each electrode between a positively connected state, a grounded state, and a disconnected state. In still other embodiments, three electrodes form a terminal. In such embodiments, two of the electrodes may be grounded, and the third electrode, which is positioned between the two grounded electrodes, may be a positive electrode connected to a signal generator. The electrodes are positioned such that the positive electrode will close a circuit with the two negative (grounded) electrodes of the same terminal. Such a design may position the center of stimulation at the location of the positive electrode.

In some embodiments, the system includes at least one sensor. Optionally, the sensor is provided on the medical intubation device distally to the at least one stimulator. Optionally, the sensor is a pH sensor, optionally adapted to sense a change (e.g., decrease) of local pH, for example due to the presence of gastric contents proximally to the LES. Optionally, alternatively or additionally, an impedance sensor may be used, configured for sensing a change in impedance of tissues provided between stimulators and/or electrodes, optionally correlative to a reaction to gastric contents or other substances. Optionally, alternatively or additionally, other sensor types may be used, including but not limited to a pressure sensor, a manometer, a moisture sensor, a temperature sensor, a motion sensor, a capacitance sensor and a mechanical sensor.

In an aspect of some other embodiments, there is provided a method for generating esophageal peristalsis in a patient intubated with a gastric tube. In some embodiments, the method comprises at least one of the following steps, optionally with no particular order:

1. positioning at least two electrodes, including one or more proximally positioned electrodes and one or more distally positioned electrodes, at spaced positions along the gastric tube, where the positions are selected such that after installation of the gastric tube, the at least two electrodes will be between the upper esophageal sphincter (UES) and the lower esophageal sphincter (LES);
2. electrically connecting the at least two electrodes to a generator; and/or
3. generating a signal sequence including a first signal at the proximally positioned electrode thereby stimulating a proximal esophageal tissue and a second signal at the distally positioned electrode thereby stimulating a distal esophageal tissue.

In some embodiments, the electrodes apply electrical current in a series of one or more electrical trains (also referred to herein as pulse groups), wherein each train is composed of a series of cycles, and each cycle includes one pulse. Pulses within a train or pulse group are characterized by an interpulse spacing, and different pulse groups are separated by an intergroup spacing. Generally, the interpulse spacing between pulses within a group or train is less than the intergroup spacing between at least some groups. Each electrical pulse has an amplitude; in preferred embodiments, the amplitude is higher than a stimulating threshold, wherein the stimulating threshold is the minimum voltage at which a local contraction occurs when applied to a portion of the esophagus. In some embodiments, the stimulating threshold is between 5V and 20V, optionally between 8V and 10V or between 10V and 15V; in other embodiments, the stimulating threshold may be higher or lower than said values. Each pulse is provided for a duration of time. In some embodiments, the pulse width (i.e., the duration) is equal to or greater than 5 milliseconds, and optionally, equal to or greater than 10 milliseconds. The applied pulse is followed by a duration of lower current and/or no current. Together, one pulse and one duration of low current compose a cycle. In some embodiments, one cycle lasts 20 ms; in other embodiments, one cycle lasts 15 ms, or optionally 30 ms, or less than, greater than, or intermediate to said values. In some embodiments, multiple cycles are provided successively such that together the cycles form a train having a duration of one to two seconds. In other embodiments, trains are provided that are longer or shorter in duration. The train is then followed by a duration of no current or low current produced by below-threshold voltages.

In some embodiments, the sequence of trains or other signal sequence produces a contraction wave that travels a length of the esophagus. In some embodiments, the contractions generate or simulate natural peristalsis.

In some embodiments, before each train or pulse, one or more below-threshold pulses are applied to the tissue to prime the tissue and induce it to contract more firmly and efficiently and to begin contracting at lower voltage stimulation levels. Optionally, a preliminary, below-threshold train is applied before each stimulating train or pulse. In some embodiments, a continuous below-threshold train is applied to specific portions of the esophagus to desensitize, and thereby avoid unneeded contractions within, said portions. For example, the LES must be open in order for material to pass from the esophagus into the stomach. In one embodiment therefore, one or more electrodes may also be positioned on the gastric tube such that after installation they are adjacent the LES to provide a continuous below-threshold train which will be applied to the LES to desensitize it so that it does not contract when material arrives. Such electrode(s) may also be used to close the LES if that is a desired response under some circumstances.

In an aspect of some embodiments, there is provided a method for connecting at least one electrode to a gastric tube readily positioned in a patient's esophagus. In some embodiments, the method comprises at least one of the following steps, optionally with no particular order:

1. locating a target portion on the gastric tube at a chosen distance from a proximal end thereof;
2. providing an electrode fixator configured for fixedly covering a portion of the gastric tube, the electrode fixator comprising at least one electrode electrically connectable with a signal generator and locking means;
3. positioning the electrode fixator over the target portion; and/or
4. applying the locking means to fixedly lock the electrode fixator in place.

In some embodiments, at least one of the steps includes the use of internal and/or external imagery. Optionally, additionally or alternatively, imaging guidance, optionally including x-ray and/or RF sources, may be applied, for example, to locate the electrode and change its position on the feeding tube while in the patient. This may allow the clinician to keep the feeding tube tip in appropriate position while adjusting the location of the electrode.

In some embodiments of the invention, the fixator positioning includes a step of: sleeving the electrode fixator over and along the gastric tube. Optionally, the method further comprises a step of: partially withdrawing the gastric tube to expose the target portion.

Referring now to the drawings, FIG. 1A schematically illustrates an exemplary system 10 comprising an elongated member 11 positioned in a patient's esophagus and including a plurality of stimulators 12, in accordance with an embodiment. Elongated member 11 may be any plastic or elastic rod or tube sized to enter and be pushed through the esophagus, preferably with no injury to adjacent tissues. Elongated member may be a probe, a catheter and/or a nasogastric tube (NGT), the latter is optionally used for injecting food directly to a patient's stomach and/or pumping out chyme to relieve excessive gastric pressure. Stimulators 12 may be any mechanical, electrical or chemical local muscle or neural stimulators. Four stimulators 12 are shown for illustrative purposes, although any other number of stimulators may be provided. In some exemplary embodiments, stimulators 12 are or include at least one electrode. In some embodiments, each shown stimulator 12 represents a number of electrodes provided around a local periphery of elongated member 11. In some embodiments, stimulators 12 are provided in a sequential order, optionally having a constant or selectively changeable distance therebetween. Optionally, stimulators 12 comprise bi-polar electrodes so that pairs of adjacent non-short-circuited electrodes can be used for closing an electrical circuit and thereby stimulate an esophageal muscle tissue in-contact and in-between the two electrodes. A generator 13, optionally an electrical signal generator, is shown connected to stimulators 12 via elongated member 11, optionally over and along its outer periphery or via a lumen thereof. To produce a series of esophageal contractions in accordance with a chosen scheme or logic, such as optionally simulating a naturally occurring esophageal peristalsis, separate generator outputs may be provided to separate electrodes or electrode groups 12. In some advantageous embodiments, the spacing between electrodes or electrode groups 12 is less than 5 cm, and the distance between the most proximal electrode or electrode group 12 and most distal electrode or electrode group 12 is at least 10 cm. This allows sequential stimulation of the electrodes or electrode groups 12 along a significant portion of the esophagus between the UES and the LES.

In FIG. 1B, an exemplary system 20 is schematically illustrated comprising an oral feeding tube 21 positioned in a patient's esophagus and including a mono-polar stimulator 22, in accordance with an embodiment. Although it is commonly more safe and convenient to place an esophageal intubation via a nasal cavity, there might be circumstances (e.g., with infant patients) where a tube is inserted via the oral cavity as suggested in this figure. Mono-polar stimulator 22 is electrically connected to an outside source or ground (shown in the figure as "(−)") and is selectively capable of closing an electrical circuit with an external electrode 23, optionally positioned on the patient's neck skin. A single electrode may be used to stimulate a neutrally sensitive region thereby evoking an esophageal contraction wave from the stimulated region and downward, optionally to the LES or the stomach interim. Optionally, alternatively or additionally, a single electrode may be used for local muscle contraction in order to serve as a barrier for refluxed gastric contents and/or for decreasing overall esophagus volume and increasing esophageal pressure.

In FIG. 1C, an exemplary system 30 is schematically illustrated comprising a feeding tube 31 positioned in a patient's esophagus and including a plurality of stimulators 32 and a sensor 33, in accordance with an embodiment. Feeding tube 31 may be used to introduce partly digested food or fluids directly to the small intestine (e.g., opened at the duodenum or at the jejunum). Sensor 33 may be a pH sensor, optionally positioned adjacent or proximal to the LES or stomach entry. In the case of a substantially low pH, such as in the presence of acid refluxed chyme, sensor 33 automatically signals and/or initiates the stimulations protocol for electrodes 32 to force the gastric content to flow back towards the stomach. In cases where no sensor is present, different stimulation protocols may apply, for example continuous stimulation regimes in which different electrodes are used sequentially to stimulate local tissues at specific frequencies and magnitudes. Optionally, alternatively or additionally, a local esophageal contraction or spasm is evoked, for any chosen duration, to act as a local physical barrier, thereby preventing or diminishing refluxed substance from passing therethrough. Such a local contraction/spasm may be singular or generated at different occasions and/or portions of the esophagus.

Figure 2B:
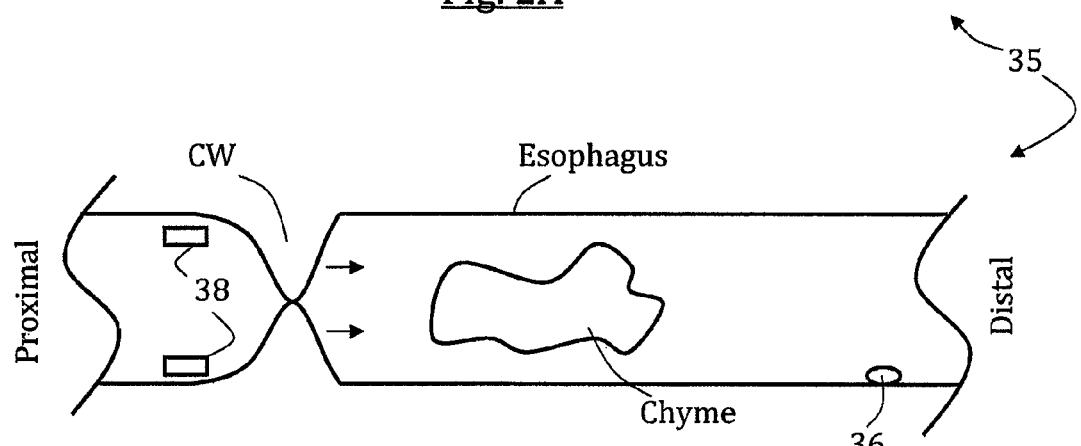
Figure 2C:
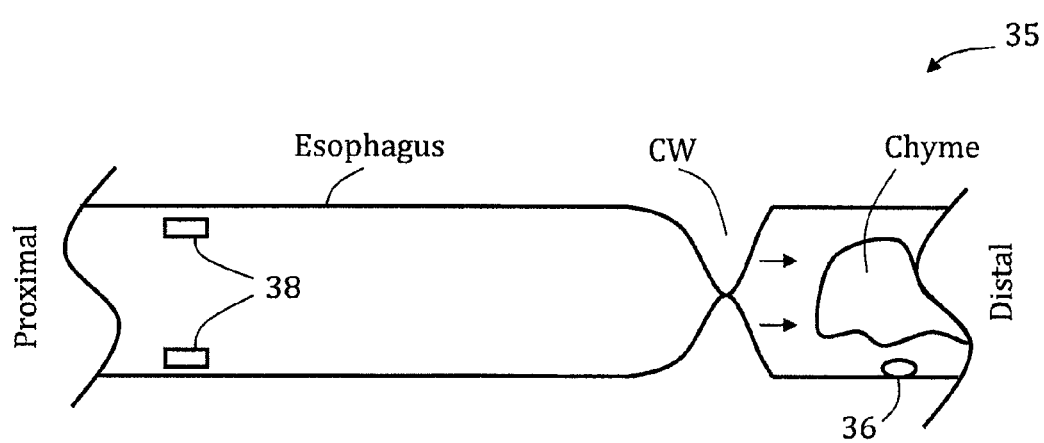
Figure 3B:
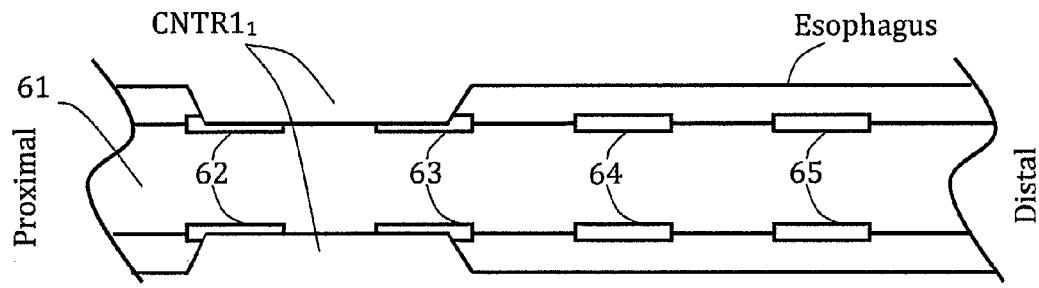
Figure 3C:
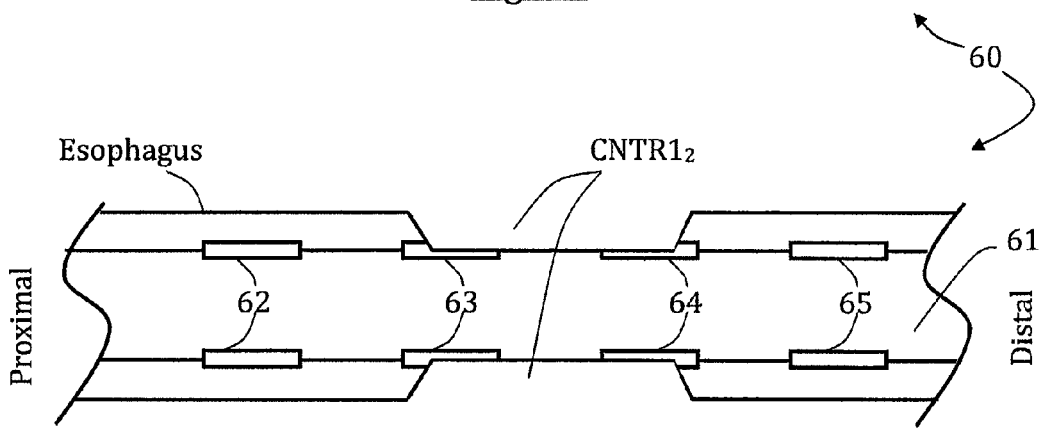
Figure 3D:
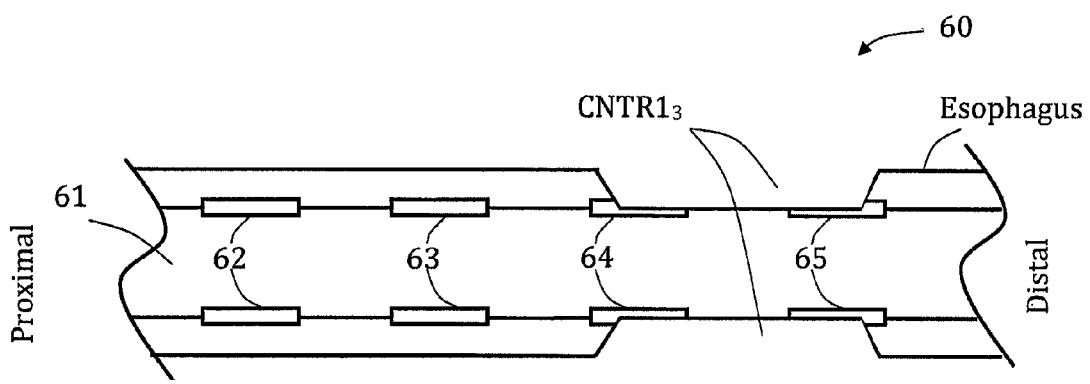
Figure 4B:
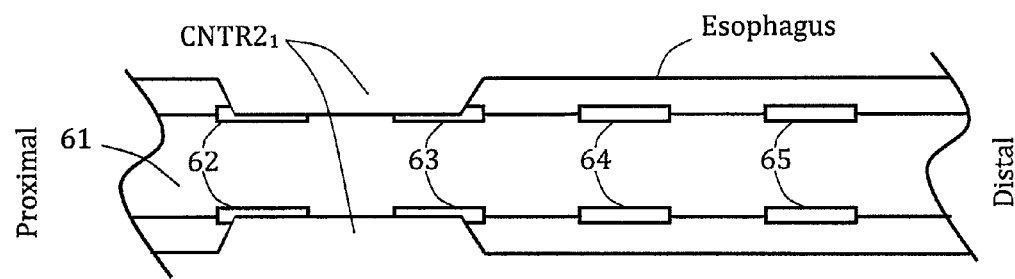
Figure 4C:
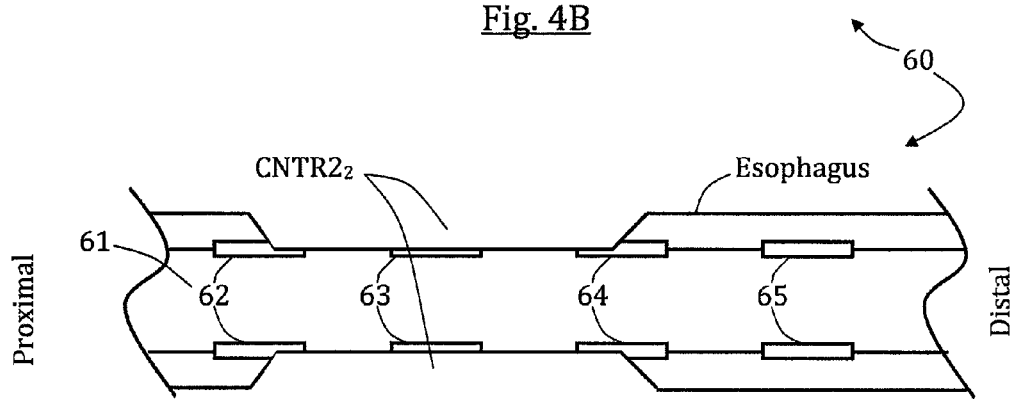
Figure 4D:
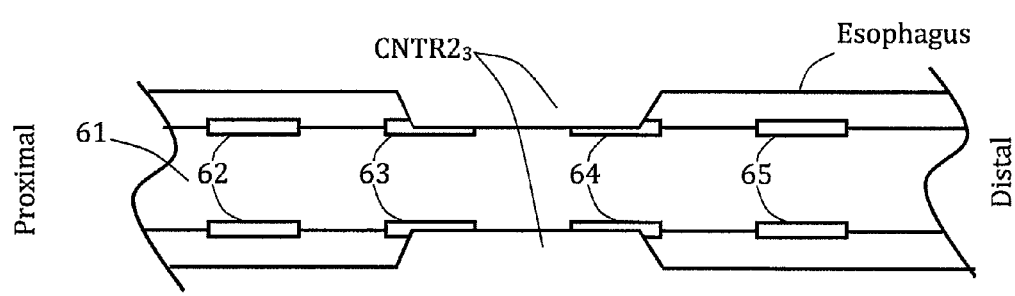

Reference is now made to FIGS. 2A-C which schematically illustrate a partial cut view of a contraction wave stimulating system 35 provided in an esophagus, shown at different operation stages, in accordance with some embodiments. As shown in FIG. 2A, in one embodiment, a gastric content or chyme travels proximally away from the stomach adjacent to a pH sensor 36 previously deployed in the esophagus. Once a pH change is sensed, proximally positioned stimulators 38 initiate a stimulation having a magnitude and/or frequency adapted to evoke a distally advancing esophageal contraction wave capable of pushing back the chyme. As shown in FIGS. 2B and 2C, a contraction wave CW is created by adjacent stimulators 38 and moves distally while pushing the chyme back towards the stomach. Optionally, CW simulates a naturally occurring esophageal peristalsis, although the motion may be different from natural peristalsis in at least one factor, for example, in magnitude, speed and/or frequency.

Reference is now made to FIGS. 3A-D which schematically illustrate a first exemplary stimulation sequence 40 and a correspondingly generated patterned esophageal motion, using a stimulation system 60, in accordance with some embodiments. As shown, system 60 includes a catheter 61 extending across a length of the esophagus and a plurality of bi-polar stimulation electrode pairs, including a proximal-most electrode 62, then electrode 63, electrode 64 and electrode 65. In this embodiment, each electrode encircles the catheter. Stimulation sequence or protocol 40 generates a combination of signals through different channels, including a channel 42 adapted to stimulate an esophageal muscle tissue provided between electrodes 62 and 63, a channel 44 adapted to stimulate an esophageal muscle tissue provided between electrodes 63 and 64, and a channel 46 adapted to stimulate an esophageal muscle tissue provided between electrodes 64 and 65. As shown, channel 42 stimulates the esophagus with voltage V at duration $\Delta T1_1$ thus evoking a local contraction $CNTR1_1$ at the same duration. Immediately following, channel 44 stimulates the esophagus with voltage V at duration $\Delta T1_2$ thus evoking a second local contraction $CNTR1_2$ at the same duration. This is followed by stimulation through channel 46 with voltage V at duration $\Delta T1_3$, which evokes a third local contraction $CNTR1_3$ at the same duration.

FIGS. 4A-D schematically illustrate a second exemplary stimulation sequence 50 and a correspondingly generated patterned esophageal motion, still using stimulation system 60, in accordance with some embodiments. This time two channels, 52 and 54, are shown with corresponding stimulation durations $\Delta T2_1$ and $\Delta T2_3$ that are overlapping at partial duration $\Delta T2_2$. This way, a traveling contraction wave simulates a general peristaltic motion in which a first local contraction $CNTR2_1$ extends distally to become $CNTR2_2$ and only afterwards diminishes to leave a distal local contraction $CNTR2_3$.

Figure 5A:
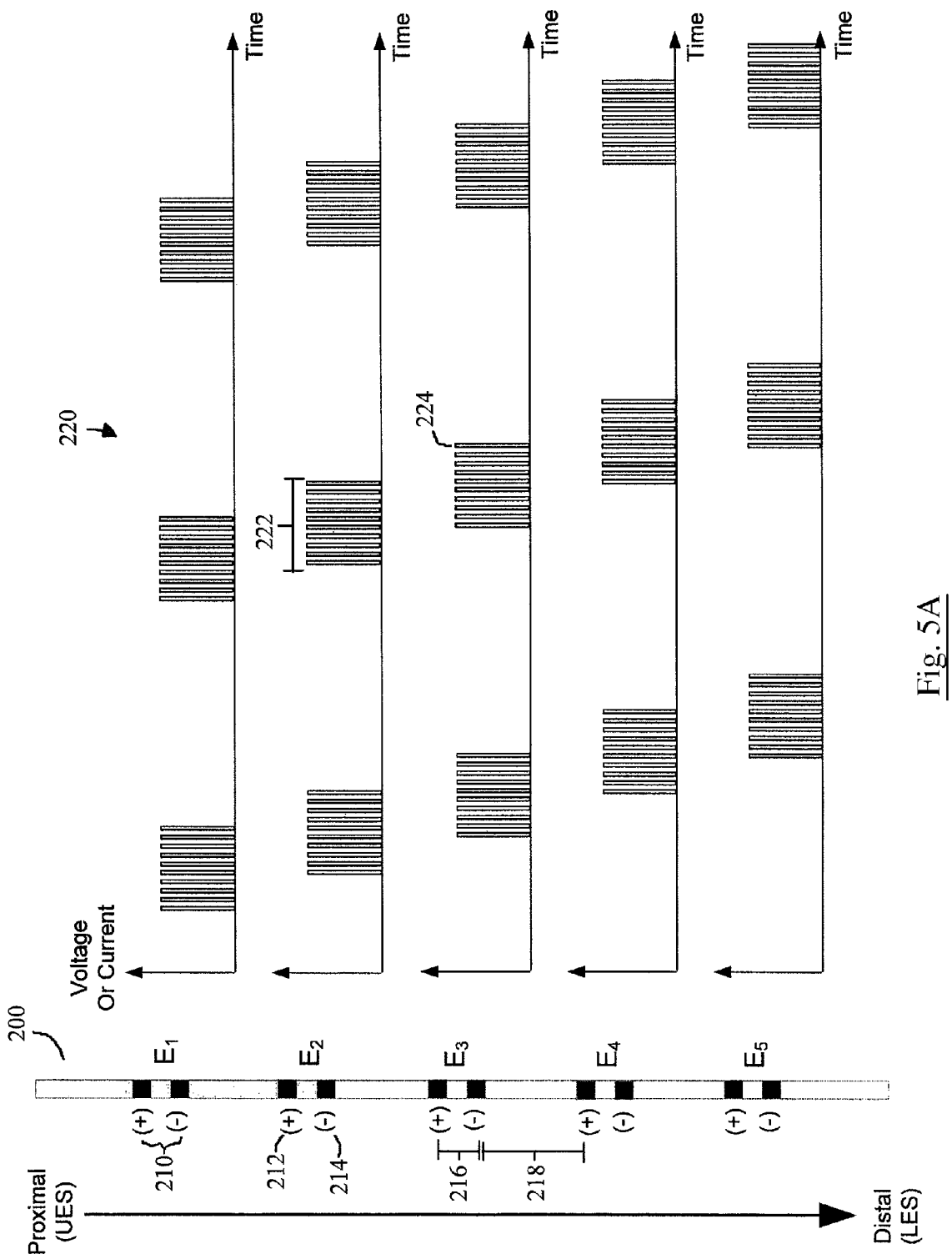
FIG. 5A schematically illustrates a top view of an exemplary esophageal intubation tube provided with a plurality of terminals comprising two electrodes each; an exemplary signal sequence from each terminal is also illustrated, in accordance with some embodiments of the present invention.
Figure 5B:
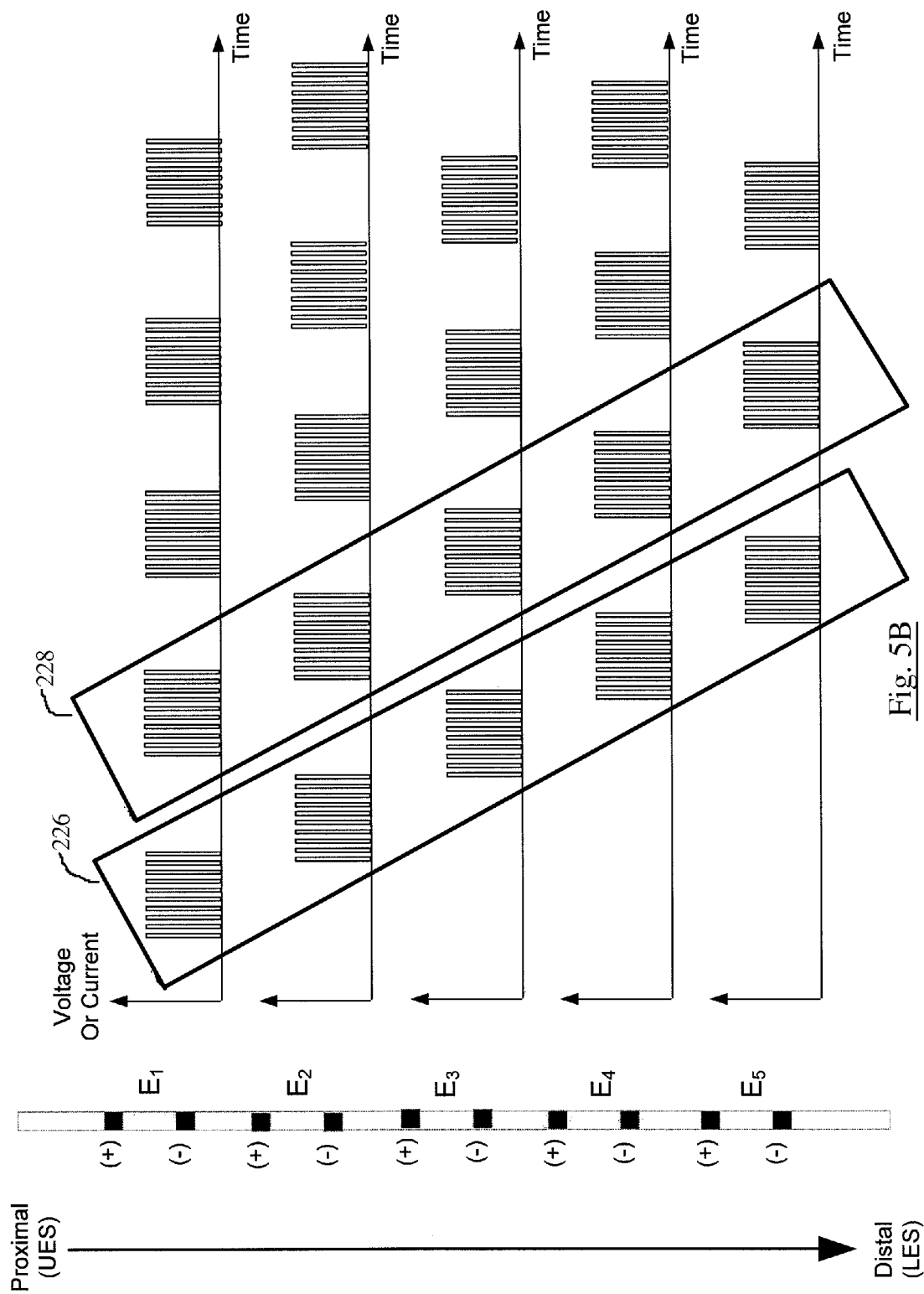
FIG. 5B schematically illustrates a top view of an exemplary esophageal intubation tube provided with a plurality of terminals comprising two electrodes each; an exemplary signal sequence from each terminal is also illustrated, in accordance with some embodiments.

FIG. 5A schematically illustrates an exemplary esophageal intubation tube 200 provided with a plurality of terminals 210 comprising two electrodes each: a positive electrode 212 and a negative (grounded) electrode 214, in accordance with some embodiments. The electrodes are spaced such that the distance 218 between each terminal is greater than the distance 216 between each electrode within any given terminal. As used in this application, whenever a distance between electrodes is mentioned, the center to center distance is being referred to. The electrodes 212 and 214 of each terminal 210 are connected to a remote electrical signal generator via electrical circuitry (not shown). A current or voltage, optionally a pulsed current or voltage, is provided to the positive electrode 212. An exemplary signal sequence 220 is also illustrated in FIG. 5A. As shown, a train 222 of pulses 224 is provided to each terminal 210. In some embodiments, the signal sequence 220 is staggered in time such that distally-located terminals receive stimulating trains 222 after more proximally-located terminals. By providing a plurality of terminals 210 receiving staggered signal sequences, a wave of contractions, optionally simulating peristalsis, may be generated. In this example there are three "waves" of stimulations that progress down the esophagus and a second wave starts only after the first wave is finished (with no overlapping). A different approach is seen in FIG. 5B, where a second wave 228 starting at the upper portion of the esophagus begins before a first wave 226 of stimulations down the esophagus is completed. In this implementation, there may be two distant esophagus portions which contract at the same time. This may increase overall peristalsis efficacy, while better overcoming still retrograding material that managed to "infiltrate" through distal contractions/waves.

Figure 6:
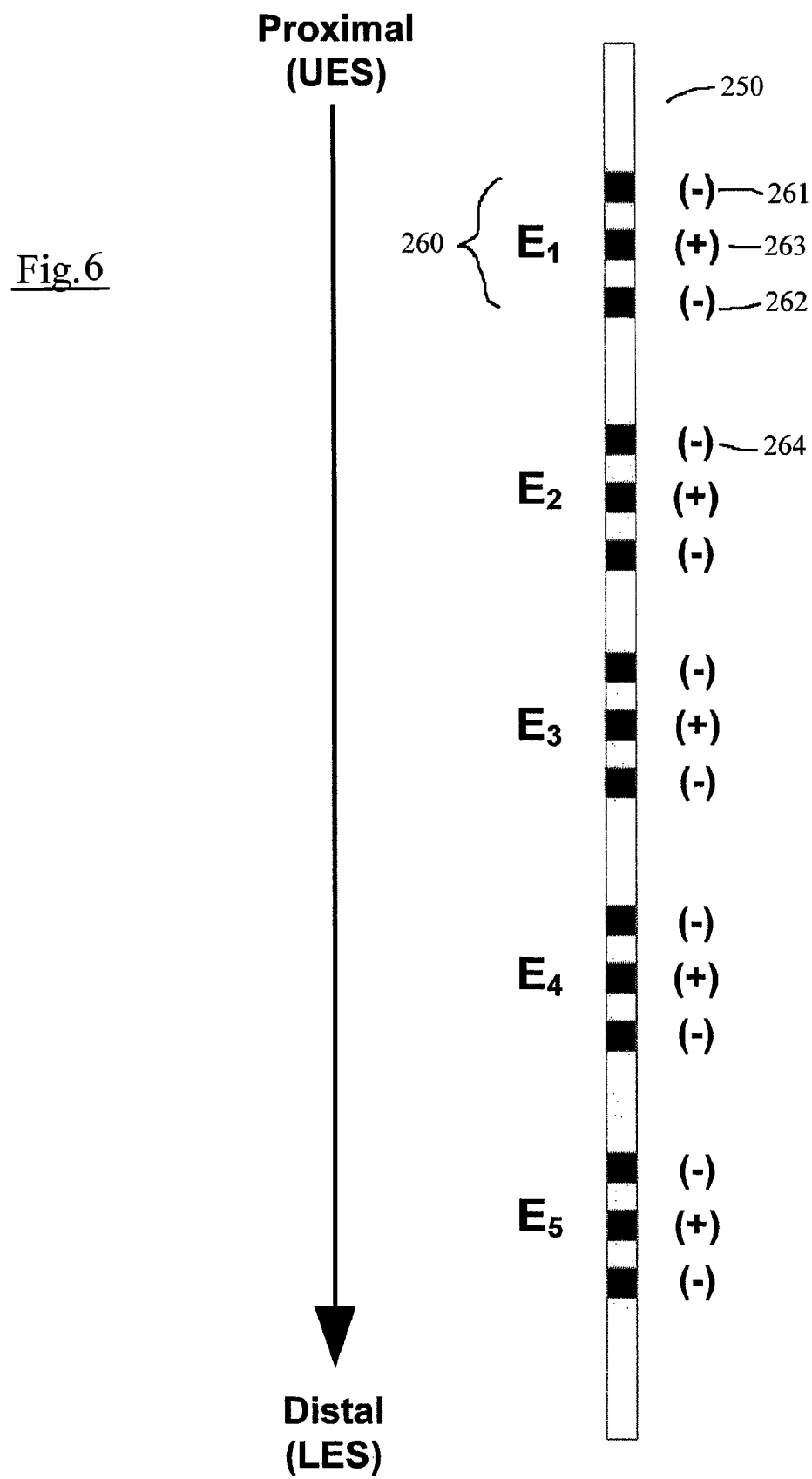
FIG. 6 schematically illustrates a top view of an exemplary esophageal intubation tube provided with a plurality of terminals comprising three electrodes each, in accordance with some embodiments of the present invention.

Another exemplary esophageal intubation tube 250, illustrated schematically in accordance with some embodiments, is provided in FIG. 6. The esophageal intubation tube 250 is provided with a plurality of terminals 260 comprising three electrodes each. In some embodiments, each terminal includes one positive electrode 263 and two negative electrodes 261 and 262 on either side of the positive electrode 263. With such a configuration, the positive electrode 263 of a terminal is positioned far closer to the negative electrodes 261 and 262 of the same terminal, at both directions, than to any other negative electrodes (e.g., 264). Such a configuration allows for a more controlled discharge of current and a more controlled area of stimulation. In some embodiments, the positive electrode 263 is located equidistant to both negative electrodes 261 and 262 within a terminal 260, thereby centering stimulations at the location of the positive electrode 263. The same stimulation protocol of FIG. 5 can be used with the electrodes of FIG. 6 where each terminal 260 has two grounded (or other low potential) electrodes rather than one.

Figure 7:
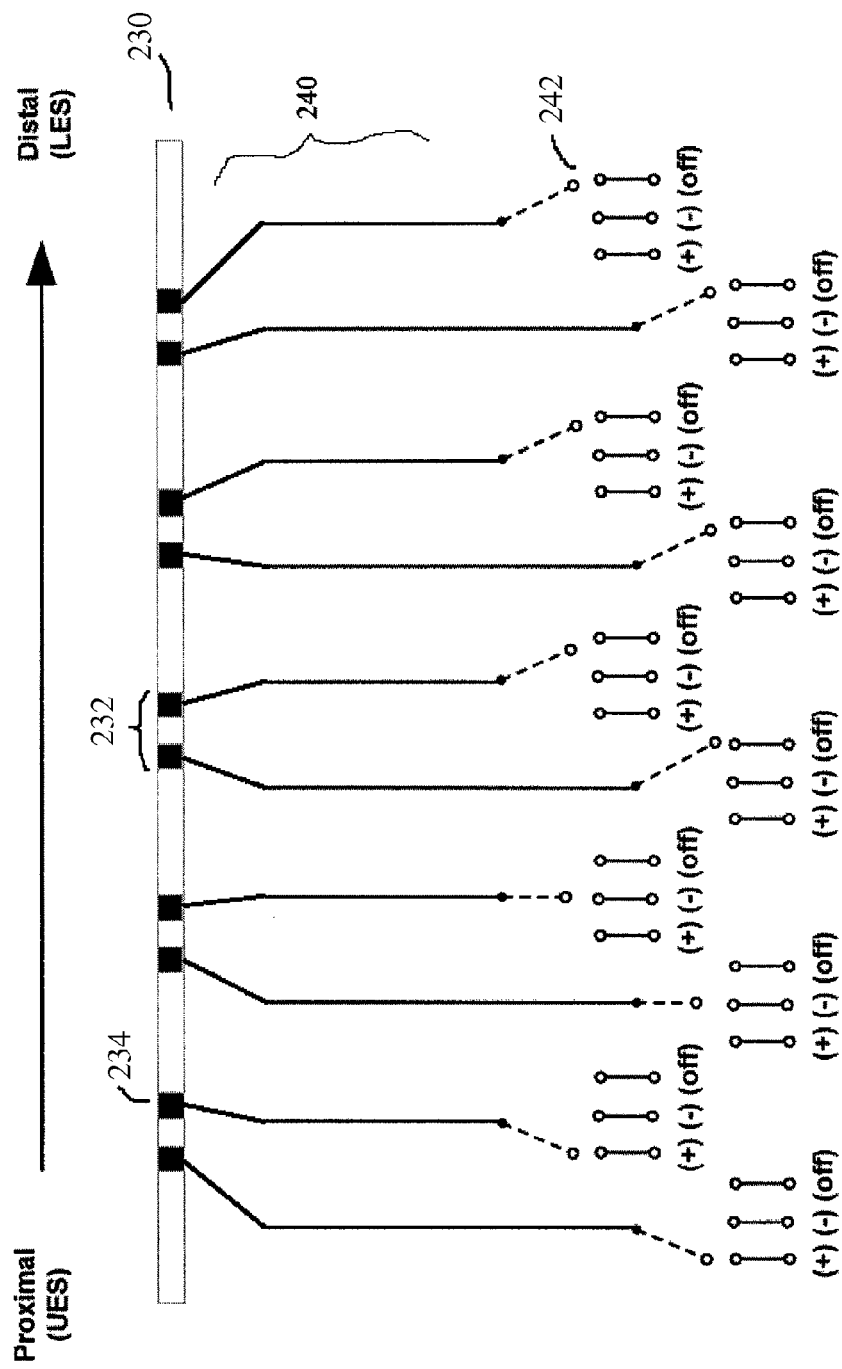
FIG. 7 schematically illustrates a top view of an exemplary esophageal intubation tube that is provided with a plurality of terminals comprising two electrodes each and is coupled to an array of switches, in accordance with some embodiments of the present invention.

In FIG. 7, an exemplary esophageal intubation tube 230 is schematically illustrated having a plurality of terminals 232 comprising two electrodes 234 each. In accordance with some embodiments, the esophageal intubation tube 230 of FIG. 7 is coupled to an array 240 of switches 242. In one embodiment, the array 240 of switches 242 electrically connects each electrode 234 to a signal generator or a grounding source or leaves the electrode 234 disconnected. Each electrode 234 is configured to selectively transition between each of the three states (connected to the signal generator, connected to ground, and disconnected), as directed by the array 240. By selectively transitioning the electrodes between the various connected states, the area of stimulation can be changed.

Figure 8:
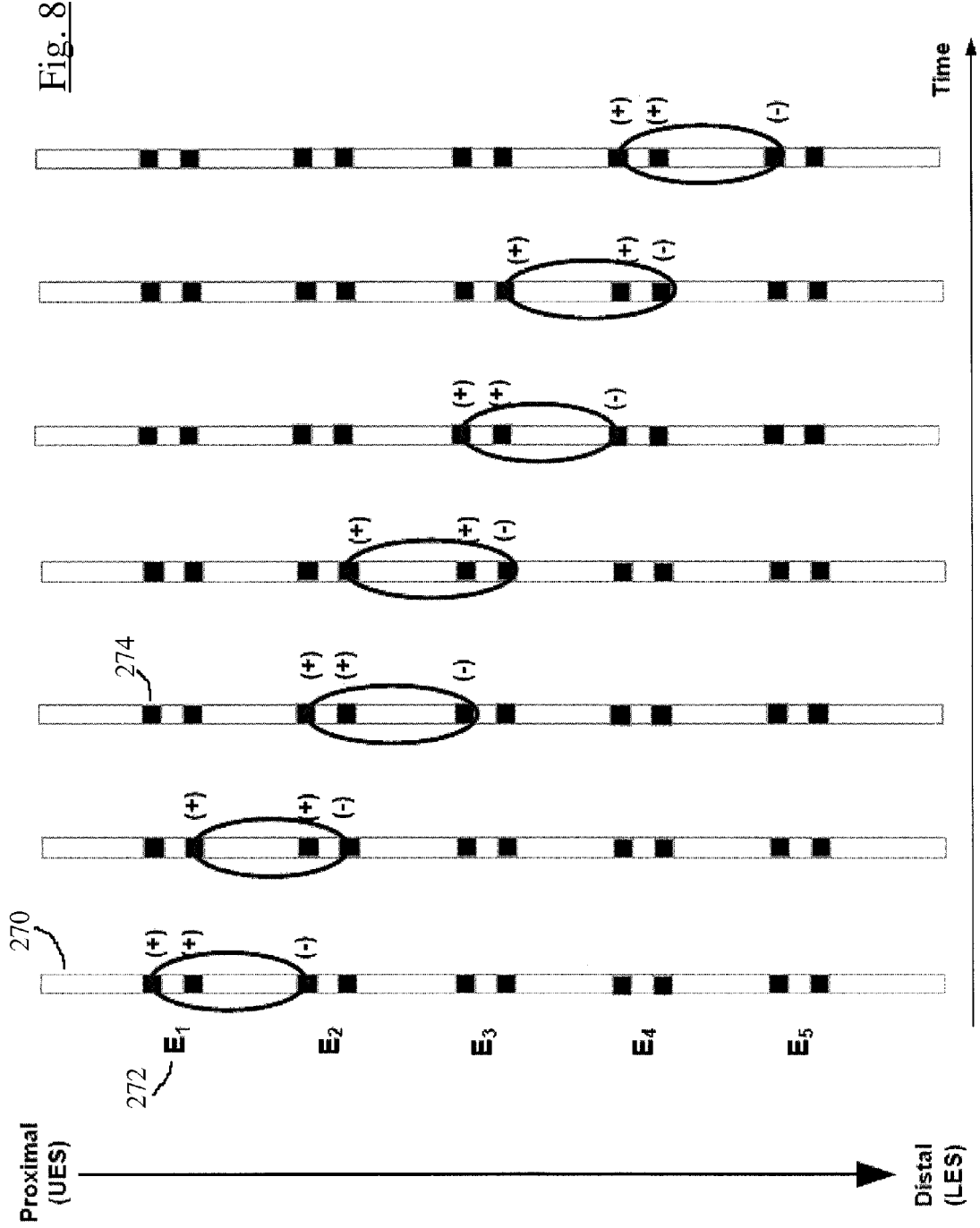
FIG. 8 schematically illustrates a top view of an exemplary esophageal intubation tube having a plurality of electrodes with polarities modulating over time to create a stimulation sequence, in accordance with some embodiments of the present invention.

FIG. 8 schematically illustrates the polarity of various electrodes 274 modulated over time, wherein the electrodes 274 are positioned on an exemplary esophageal intubation tube 270, in accordance with some embodiments. In the embodiment of FIG. 8, the electrodes are arranged into terminals 272 at spaced positions along the length of the esophageal intubation tube 270 between the UES and the LES. Each electrode 274 on the esophageal intubation tube 270 may be coupled to an array of switches (such as shown in FIG. 7).

Figure 9:
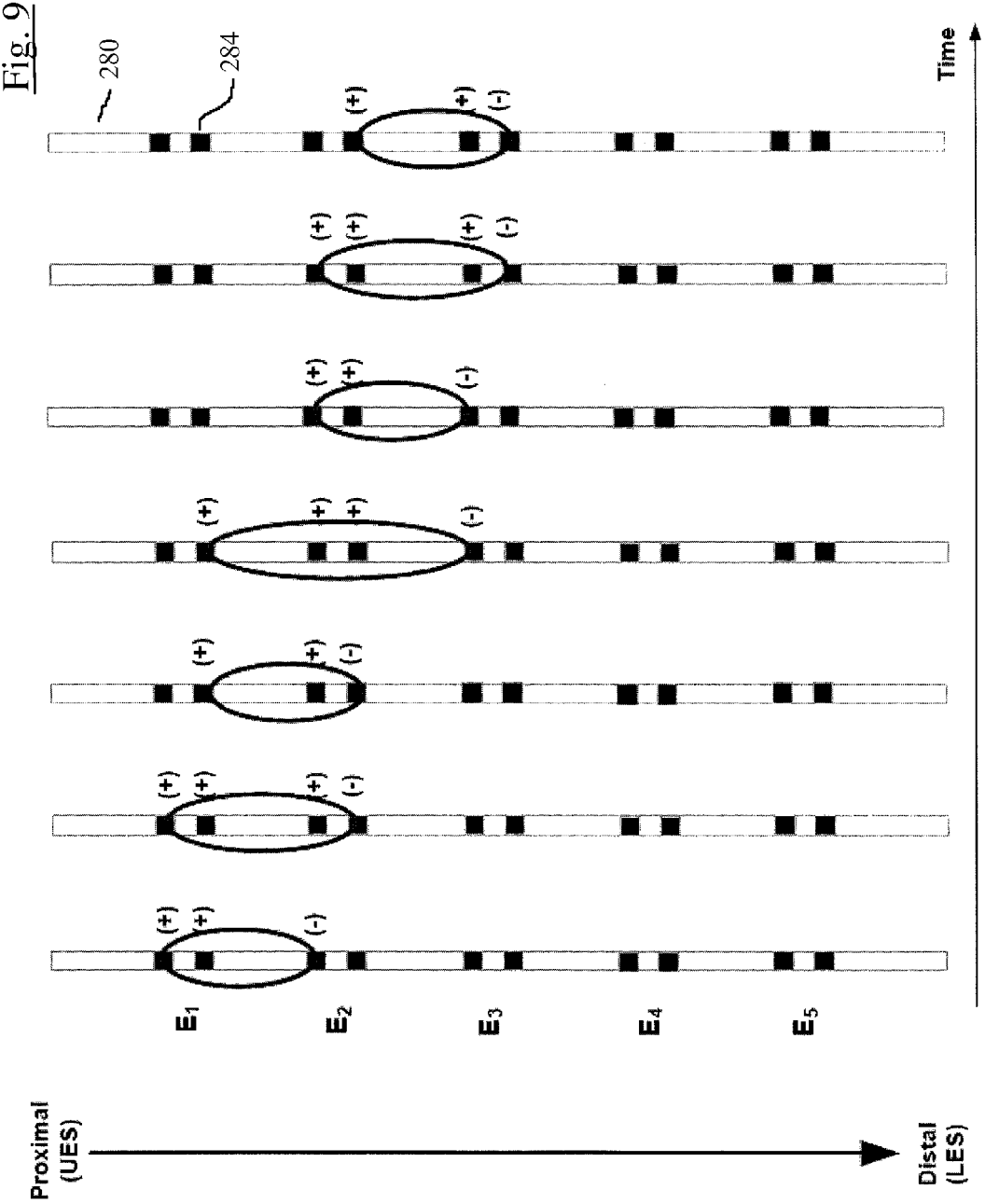
FIG. 9 schematically illustrates a top view of an exemplary esophageal intubation tube having a plurality of electrodes with polarities modulating over time to create another stimulation sequence, in accordance with some embodiments of the present invention.

With such an arrangement, the polarity of the electrodes 274 can be modulated over time, as directed by the array of switches, to generate a sequence of voltage applications. One potential sequence of voltage applications is provided in FIG. 8; however, any sequence may be applied, and all such sequences are contemplated herein. As depicted, all electrodes with "(+)" located beside them are receiving a voltage from a signal generator; the electrode having "(−)" beside it is grounded (or at another low potential); and all electrodes without a symbol are disconnected from the signal generator. The general area of stimulation at each depicted time is represented by the drawn ellipses. As shown, the area of stimulation may be controlled and changed over time. This is one way to produce a distally traveling wave while controlling the "length" of the stimulated portions. Here, the length is chosen between proximal-most "+" and distal Similarly, FIG. 9 schematically illustrates the polarity of various electrodes 284 modulating over time, wherein the electrodes 284 are positioned on an exemplary esophageal intubation tube 280, in accordance with some embodiments. FIG. 9 illustrates another potential sequence of voltage applications provided to produce an exemplary wave of distally-progressing contractions within the esophagus. The degree of spatial overlapping between stimulations need not be coherent. For example, in first change of polarity there is substantial overlap, then small overlap, then substantial overlap, etc.

Figures 10A, 10B:
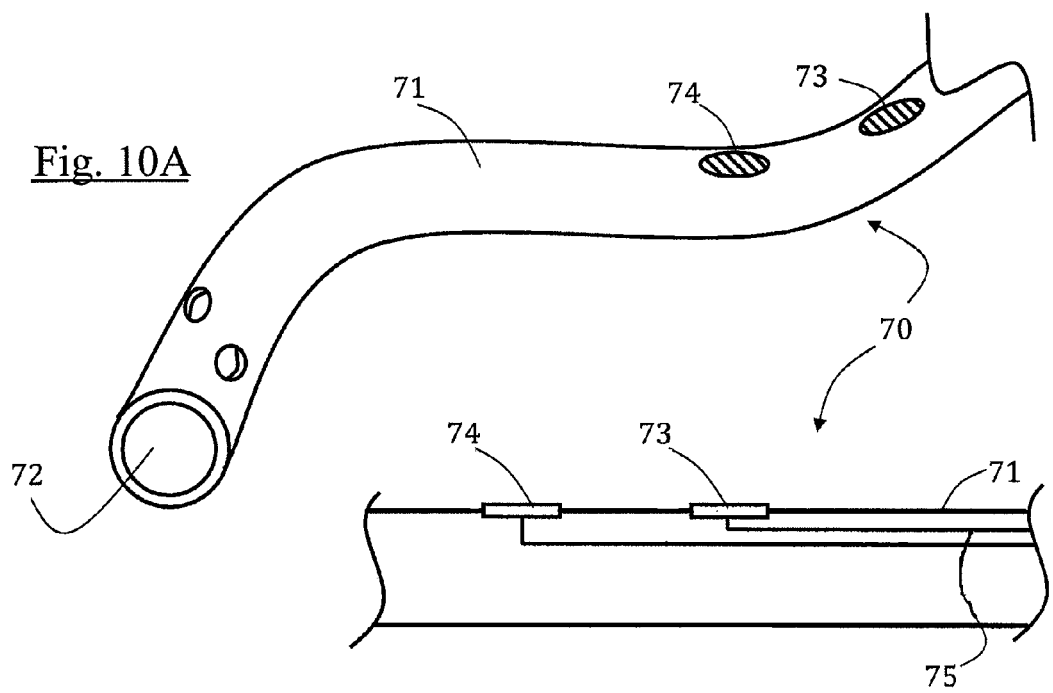
FIGS. 10A-B schematically illustrate a partial isometric view and a partial top view of an exemplary NG tube provided with a plurality of electrodes, in accordance with some embodiments of the present invention.

Reference is now made to FIGS. 10A-B which schematically illustrate a partial isometric view and a partial top view of an exemplary stimulating system 70 comprising an NG tube 71 and a plurality of electrodes 73 and 74, in accordance with some embodiments. Electrodes 73 and 74 are connected to a remote electrical signal generator (not shown) via electrical circuitry 75 provided over NG tube 71 or embedded in its wall. Electrodes 73 and 74 may fully or partially encircle the circumference of the tube 71. Opening 72 is provided at the lower end to deliver food and other nutrients to the stomach.

Figures 11A, 11B:
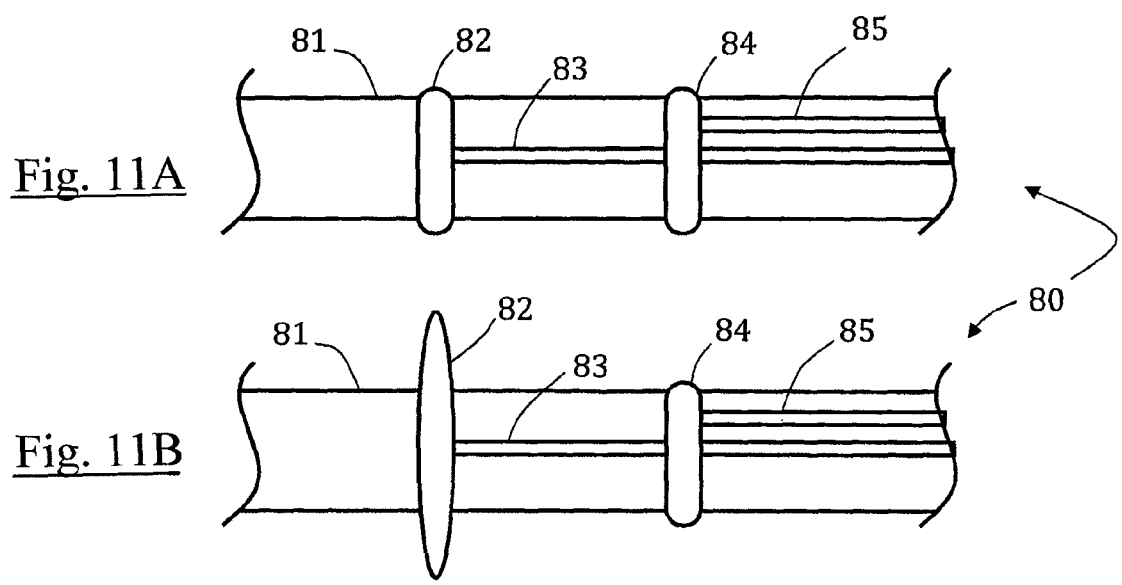
FIGS. 11A-B schematically illustrate a partial top view of an exemplary NG tube provided with a plurality of expandable stimulators, before and after actuation, in accordance with some embodiments of the present invention.

An alternative stimulator system 80 is shown in FIGS. 11A-B, which schematically illustrate a partial top view of system 80 comprising an NG tube 81 and a plurality of expandable stimulators 82 and 84, before and after actuation, in accordance with some embodiments. In some exemplary embodiments, stimulators 82 and/or 84 are inflatable, and optionally toroidal shaped balloons, which encircle portions of the NG tube 80. The distal expandable stimulator 82 is optionally connectable to a remote pump (not shown) via line 83, whereas the proximal stimulator 84 is optionally connectable to the pump via line 85. Lines 83 and/or 85 may be hydraulic or pneumatic lines configured to provide pressurized media from the pump into stimulators 82 and/or 84, correspondingly. Optionally, the pumped medium is provided in a pulsatory fashion. In FIG. 11B, stimulator 82 is shown in a maximally expanded form. In some embodiments, stimulator 82 may expand to a predetermined and/or limited shape and/or size, which causes an esophageal tissue in contact to radially stretch open in order to evoke a natural downward peristalsis, and optionally, to simulate a spontaneous naturally occurring peristalsis.

Figure 12:
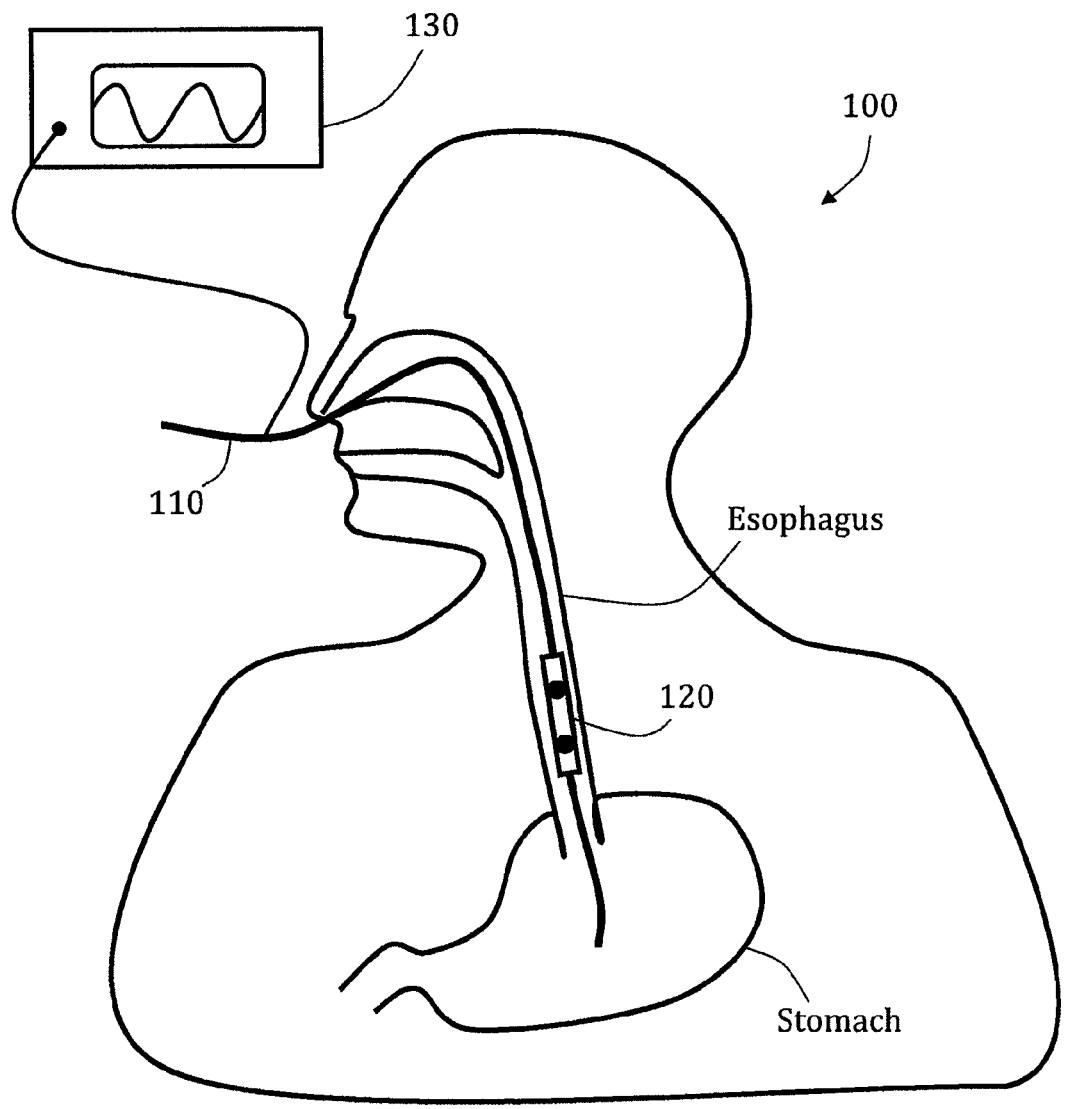
FIG. 12 schematically illustrates an exemplary NG tube positioned in a patient's esophagus and provided with a fixedly positioned stimulator fixator, in accordance with some embodiments of the present invention.

In some instances it may be advantageous to add a stimulating device over an existing intubation tube nested in a patient's esophagus, as for example in a patient entering ICU with an NGT in place. FIG. 12 schematically illustrates an exemplary system 100 which comprises an NGT 110, positioned in a patient's esophagus and provided with a fixedly positioned stimulator fixator 120, in accordance with some embodiments. The fixator 120 includes at least one stimulator (e.g., a balloon type or electrode-type) and is shown connected to a remote generator 130. The fixator 120 may be pushed along a length of the NGT 110 to a chosen distance or esophagus portion. Optionally, alternatively or additionally, the NGT 110 is partially withdrawn, optionally until a target NGT portion is expelled from the body and/or is conveniently reachable to place the fixator 120 thereto. The fixator 120 may be sleeved along the NGT 110, or it may be a cuff-type fixator, deployable to restrictively compress the at least one stimulator in place along the NGT 110.

FIGS. 13A-D schematically illustrate different exemplary fixators, in accordance with some embodiments. In FIG. 13A, an elongated slitted sleeve 131 is shown, partially covering a proximal portion of an NGT, including a plurality of electrodes 133 electrically connectable to a remote source (e.g., an electrical signal generator) via a cord 134. The slitted sleeve 131 includes a slit 132 across its entire length, thereby facilitating its fixation to the NGT without a need to substantially widen it before. In some embodiments, the slitted sleeve 131 is self-contractible in a way that totally avoids movement along the NGT once fixated thereto. FIG. 13B shows a different exemplary embodiment in which electrodes are fixated to an NGT using distinct cuff-like fixators: a distal electrode 142 is fixed to the NGT using a fixator 141, and a proximal electrode 144 is fixed to the NGT with a fixator 143. A cord 145 connects the electrodes to a remote signal generator (not shown). FIGS. 13C and 13D show transverse cross-sections of different cuff-like stimulator fixators 150 and 155, correspondingly. The cuff-like fixator 150 includes a body 151, two opposing electrodes 152 connectable to a remote generator by a cord 153. A locking means 154 is provided in body 151 in the form of a snap-lock. When the locking means 154 is opened, the fixator 150 allows slippage over a standard sized NGT, and when locked it is restricted in place, and may optionally slightly constrict the NGT portion it is confined to. The cable-tie type fixator 155 similarly includes a body 156 housing two opposing electrodes 157 connectable to a remote generator with a cord 158. Unlike the fixator 150, the fixator 155 includes a cable-tie type fastener 159 (comprising a gear-rack member and a ratchet member) as the locking means, allowing an operator to adjust the tightness of the fixator to adequately fixate the electrodes in place. In some exemplary embodiments, the deformation of the NGT as a result of the cuffing ensures a substantial grip and/or friction to disable any movement of the cuff along the tube, while preferably not restricting the NGT's inner lumen to a smaller diameter. In some embodiments, the cuffing narrows the diameter of the NGT's inner lumen by no more than 10% of its cross-section.

Figure 14A:
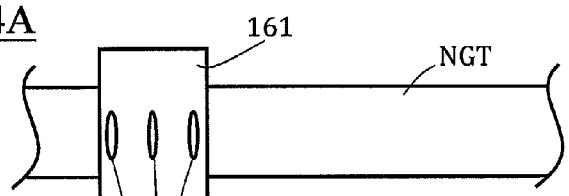
FIGS. 14A-B schematically illustrate an exemplary stretchable sleeve-type fixator, in accordance with some embodiments of the present invention.
Figure 14B:
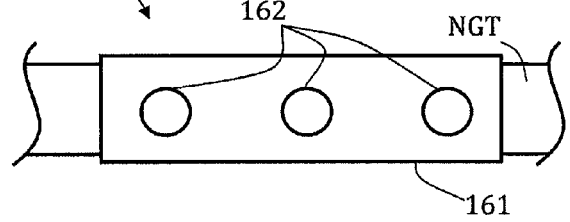

FIGS. 14A-B schematically illustrate an exemplary stretchable sleeve-type fixator 160, in accordance with some embodiments. The fixator 160 includes a stretchable tubular body 161 and a plurality of electrodes 162. In FIG. 14A, the fixator 160 is shown compressed and having an optional radially expanded form which allows it to be easily sleeved about an NGT portion, whereas in FIG. 14B, it is stretched open over most of the NGT portion and confined from stretching further by the NGT's diameter. In some embodiments, the fixator body 161 is braided from elastic fibers, either polymeric and/or metallic. Optionally, the body 161 is self-elongating. In some embodiments of the invention, an operator (e.g., a medical staff member) pushes the compressed fixator 160 over the NGT until reaching a chosen position and then releases it to stretch open in place. Optionally, the operator further stretches the fixator 160 to plastically deform a portion thereof and thereby further fixate it in place.

Figure 15:
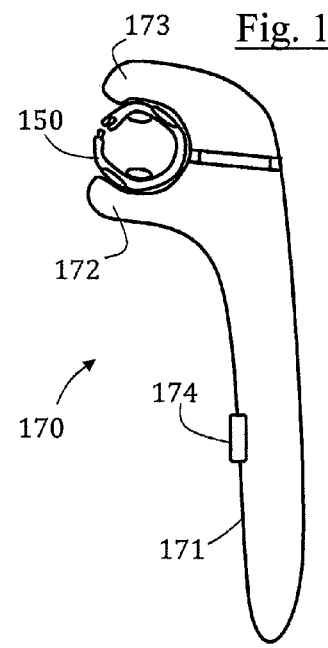
FIG. 15 schematically illustrates an exemplary delivery device for delivering fixators to a feeding tube, in accordance with some embodiments of the present invention.

Reference is now made to FIG. 15 which schematically illustrates an exemplary delivery device 170 for delivering fixators, such as the cuff-like fixator 150, to a feeding tube (not shown), in accordance with some embodiments of the present invention. The delivery device 170 includes a hand-held body 171 and two opposing jaws 172 and 173, axially movable relative to each other. A trigger 174 is manually operable to decrease a distance between jaws 172 and 173 from a first wider distance, in which the fixator 150 is maintained in an open state, to a second narrower distance, in which the fixator 150 is forced to compress and lock. Optionally, the first wider distance and/or the second narrower distance are predetermined and/or programmable. In some embodiments, the delivery device is configured to grab and fixate a fixator in a sequential manner, whereas in other embodiments, the delivery device may be housing a cartridge filled with fixators and is applicable for stapling fixators in sequence until the cartridge is emptied. The delivery device 170 may be reusable and may be configured to allow for replacing singular fixators or fixator cartridges. Alternatively, the delivery device 170 may be configured for disposable single usage. The delivery device 170 may include a mechanical, electrical and/or electromechanical mechanism (not shown) to operate the stapling following triggering. Optionally, the delivery device 170 includes a safety mechanism (not shown).

Figure 16:
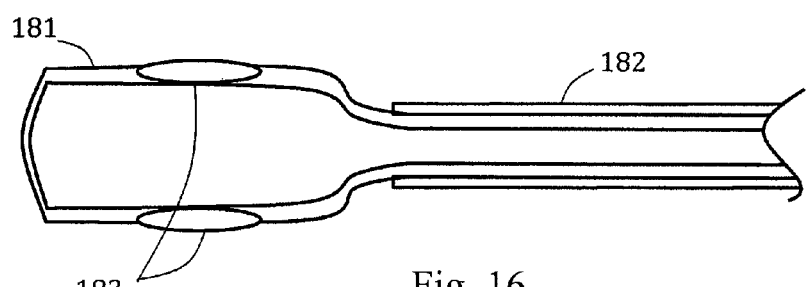
FIG. 16 schematically illustrates a partial cut view of an exemplary self-expandable electrode fixator partially emerging from a delivery catheter, in accordance with some embodiments of the present invention.

A stimulator fixator may be deployed to radially expand against the esophagus inner walls instead of compressing onto a tube or being provided as a radially non-compliant member (e.g., a probe or a catheter). FIG. 16 schematically illustrates a partial cut view of an exemplary self-expandable electrode fixator 180 partially emerging from a delivery catheter 182, in accordance with some embodiments of the present invention. As shown, fixator 180 includes a radially elastic body 181, self-expandable from a smaller confined diameter to a final fully expanded diameter. A plurality of electrodes 183 are fixated to body 181 in a manner that does not damage its ability to expand as needed. Fixator body 181 is delivered in a confined smaller diameter in delivery catheter 182 thereby allowing an easier advancing in the esophagus. Once in place, catheter 182 may be withdrawn, leaving in place fixator 180, and allowing it to gradually expand until complete removal. In some embodiments, fixator body 181 is configured to freely expand up to a diameter that is greater than the inner diameter of the esophagus, therefore it is kept securely in place by continuously applying expansive forces towards the surrounding esophagus walls.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference constitutes prior art. To the extent that section headings are used, they should not be construed as necessarily limiting.

What is claimed is:

1. A method for generating a distally traveling synthetic esophageal motion comprising:
   identifying a patient having suspended esophageal peristaltic motility;
   placing, in an esophagus of the patient, an elongated member sized and configured for nasal or oral placement into the esophagus and a series of stimulators mounted or mountable on the elongated member, the series of stimulators including at least two longitudinally spaced electrodes, chargeable to opposite polarities, for stimulating a portion of the esophagus provided therebetween;

positioning the series of stimulators along an esophageal length between the LES and the UES of the esophagus, the series of stimulators configured to directly stimulate a series of portions of the esophagus within the esophageal length; and generating a sequence of stimulating signals to the series of stimulators to evoke a plurality of local esophageal contractions to create a distally traveling synthetic esophageal motion along the esophageal length.

2. The method of claim 1, wherein the local esophageal contractions are spasms.

3. The method of claim 1, wherein the local esophageal contractions substantially close local segments of the esophagus lumen.

4. The method of claim 1, wherein the local esophageal contractions develop local esophageal pressures of at least 50 mmHg.

5. The method of claim 1, wherein the local esophageal contractions develop local esophageal pressures of at least 100 mmHg.

6. The method of claim 1, wherein the generating a sequence of stimulating signals comprises generating at least two evoked contractions that are sequentially and/or timely generated according to a preset sequence.

7. The method of claim 1, wherein the sequence of stimulating signals are generated by a generator sized and configured for prolonged intra-oral or intra-esophageal placement.

8. The method of claim 1, wherein the elongated member is a medical intubation device.

9. The method of claim 8, wherein the series of stimulators are spaced along the effective length of the medical intubation device.

10. The method of claim 8, wherein the medical intubation device is a gastric feeding tube.

11. The method of claim 1, wherein at least one of the series of stimulators is fixed to the elongated member.

12. The method of claim 1, wherein the elongated member includes at least one sensor mounted or mountable on the elongated member.

13. The method of claim 12, wherein at least one sensor is mounted on the elongated member distally to a distal-most stimulator.

14. The method of claim 12, wherein a proximal-most sensor is positioned on the elongated member at least 5 cm distally to the distal-most stimulator.

15. The method of claim 12, wherein the at least one sensor comprises at least one of: a pH sensor, a pressure sensor, a manometer, an impedance sensor, a motion sensor, a capacitance sensor, and a mechanical sensor.

16. The method of claim 1, wherein the local esophageal contractions increase local pressures between the LES and the UES.

17. The method of claim 16, wherein the increased local pressures diminish retrograde movement of material or chyme.

18. The method of claim 16, wherein the increased local pressures force retrograded material to travel to a distal esophageal segment.

19. The method of claim 1, wherein the series of stimulating signals are staggered in time such that distally-located stimulators receive stimulating signals after more proximally-located stimulators.

20. The method of claim 1, wherein the series of stimulating signals includes at least one pulse or train comprising a magnitude higher than a stimulating threshold between 5V and 20V.

21. The method of claim 1, wherein the series of stimulating signals includes a below-threshold pulse to induce the tissue to contact more firmly.

22. The method of claim 1, wherein the series of stimulating signals induces at least one pulse to induce the tissue to contact more firmly.

23. The method of claim 1, wherein the series of stimulators are configured to selectively transition between each of three states.

24. The method of claim 23, wherein the three states are connected to a signal generator, connected to ground, and disconnected from the signal generator.

25. The method of claim 1, wherein the signal sequence produces a wave of distally-progressing contractions within the esophagus.

26. The method of claim 25, wherein the wave of contractions includes a second wave starting only after a first wave is finished with no overlapping.

27. The method of claim 25, wherein the wave of contractions includes a second wave beginning before a first wave completes a travel from upper portion of the esophagus.

* * * * *